United States Patent [19]

Kubodera et al.

[11] Patent Number: 4,891,364
[45] Date of Patent: Jan. 2, 1990

[54] VITAMIN D DERIVATIVES, PROCESS FOR PRODUCING THE SAME AND THEIR USE IN THE DIFFERENTIATION OF TUMOR CELLS

[75] Inventors: Noboru Kubodera, Saitama; Katsuhito Miyamoto, Tokyo; Kiyoshige Ochi, Saitama; Isao Matsunaga, Tokyo; Eigoro Murayama, Chiba, all of Japan

[73] Assignee: Chugai Seiyaku Kabushiki Kaisha, Tokyo, Japan

[21] Appl. No.: 211,096

[22] Filed: Jun. 13, 1988

Related U.S. Application Data

[63] Continuation of Ser. No. 802,607, Nov. 25, 1985, abandoned.

[30] Foreign Application Priority Data

Nov. 27, 1984 [JP]  Japan ................................ 59-250291
Dec. 28, 1984 [JP]  Japan ................................ 59-278616

[51] Int. Cl.⁴ .......................... A61K 31/59; C07J 9/00
[52] U.S. Cl. .................................... 514/167; 260/397.2
[58] Field of Search ........................ 260/397.2, 397.5; 514/167

[56] References Cited

U.S. PATENT DOCUMENTS 4,338,250  7/1982  DeLuca et al. ................... 260/397.2
4,470,981  3/1984  Hesse ................................ 260/397.2
4,772,433  9/1988  Hesse ................................ 260/397.2

OTHER PUBLICATIONS

Pass Murari et al, "Synthesis and Biological Activity of 3β-hydroxy-9-10-secopregna-5,7,10(19)-triene-2-one; A Side Chain Analog of Vitamin $D_3$", Chem. Abstr., vol. 99, No. 5, (1983), p. 439, 37381v.
Holik et al, "Relation of 25-Hydroxyvitamin $D_3$ Side Chain Structure to Biological Activity", Chem. Abstr., vol. 82, No. 17 (1975), p. 400, 110660r.
Hing-Yat Lam et al, "Structural Analogs of 1α,25-Dihydroxycholecalciferol: Preparation and Biological Assay of 1α-Hydroxypregnacalciferol", Steroids, vol. 26, No. 4 (1975), pp. 422-436.

Primary Examiner—Douglas W. Robinson
Assistant Examiner—Joseph A. Lipovsky
Attorney, Agent, or Firm—Browdy and Neimark

[57] ABSTRACT

Vitamin D derivatives of the formula

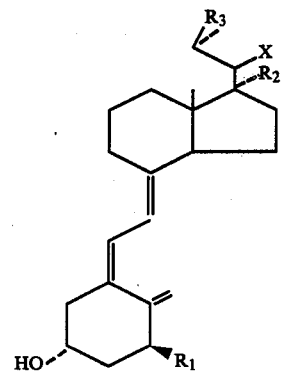

where $R_1$, $R_2$ and $R_3$ which may be the same or different each represents a hydrogen atom or a hydroxyl group; X is an oxygen atom, the group of the formula $OR_4$ (where $R_4$ is either a hydrogen atom or a lower alkyl having 4 to 6 carbon atoms that may or may not be substituted by a hydroxyl group), or the group of the formula $=N\text{-}OR_5$ (where $R_5$ is either a hydrogen atom or a lower alkyl group having 1 to 5 carbon atoms that may or may not be substituted by a hydroxyl group, an amino group or a lower alkylamino group having 1 to 3 carbon atoms), provided that the carbon atom at 20-position is linked to X by a single bond when X is the group of the formula $OR_4$, and by a double bond in other cases; and a process for preparing the derivatives are disclosed.

The derivatives have both the immunoregulating action and the ability to induce differentiation in tumor cells and hence are useful as medicines such as antiallergic agents, antirheumatic agents and antitumor agents.

23 Claims, No Drawings

VITAMIN D DERIVATIVES, PROCESS FOR PRODUCING THE SAME AND THEIR USE IN THE DIFFERENTIATION OF TUMOR CELLS

This application is a continuation of application Ser. No. 802,607, filed 11/25/85 now abandoned.

The present invention relates to vitamin D derivatives Formula (I):

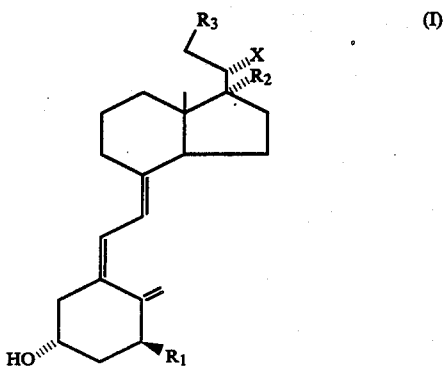

where $R_1$, $R_2$ and $R_3$ which may be the same or different each represents a hydrogen atom or a hydroxyl group; X is an oxygen atom, the group of the formula $OR_4$ (where $R_4$ is either a hydrogen atom or a lower alkyl having 4 to 6 carbon atoms that may or may not be substituted by a hydroxyl group), or the group of the formula $=N-OR_5$ (where $R_5$ is either a hydrogen atom or a lower alkyl group having 1 to 5 carbon atoms that may or may not be substituted by a hydroxyl group, an amino group or a lower alkylamino group having 1 to 3 carbon atoms), provided that the carbon atom at 20-position is linked to X by a single bond when X is the group of the formula $OR_4$, and by a double bond in other cases.

The vitamin $D_3$ derivatives of Formula (I) of the present invention have both the immunoregulating action and the ability to induce differentiation in tumor cells and hence are useful as medicines such as antiallergic agents, antirheumatic agents and antitumor agents.

Vitamin $D_3$ administered in vivo is first hydroxylated in the liver at 25-position to give 25-hydroxy vitamin $D_3$ and then hydroxylated in the kidney at 1α- or 24-position to form 1α,25-dihydroxy vitamin $D_3$ or 24R,25-dihydroxy vitamin $D_3$, respectively. As is well known, 1α,25-dihydroxy Vitamin $D_3$, one of the natural metabolites of vitamin $D_3$, and a sysnthetic analog thereof such as 1α-hydroxy vitamin D have strong activities of intestinal calcium transport and bone calcium mobilization capability, making these vitamin $D_3$ derivatives useful as drugs for treating various diseases resulting from calcium dysbolism. On the other hand, evidence is accumulating today that shows that these vitamin $D_3$ derivatives have a strong ability to induce differentiation in human or mouse myelocytic leukemia cells (Proc. Natl. Acad. Sci. U.S.A., 78, 4990 (1980) and Biochem. Biophys. Res. Commun. 102, 937 (1981)) and are useful against diseases such as rheumarthritis that result from abnormal enhancement of immunological functions (Unexamined Published Japanese Patent Application No. 26820/1981). Although these vitamin $D_3$ derivatives have desirable activities such as strong differentiation inducing ability, they also present strong effects on calcium metabolism in vivo, and depending upon the dose, they may cause hypercalcemia. Therefore, these vitamin $D_3$ derivatives are not ideal antirheumatic agents or drugs for curing tumors such as leukemia, the treatment regimen for which often requires continuous administration of high doses of the drug.

As a result of various studies made in order to develop new vitamin D derivatives that are free from the problem described above, the present inventors have found that 9,10-secopregna-5,7,10(19)-triene derivatives of Formula (I) have both an immunoregulating action and a strong ability to induce differentiation in myelocytic leukemia cells while causing minimal effects on calcium metabolism in vivo. The present inventors made further studies on this observation and have reached the present invention.

The lower alkyl group represented by $R_4$ in Formula (I) expressing the compounds of the present invention is a straight- or branched-chain alkyl group having 4 to 6 carbon atoms, and preferred examples include 2,3-dimethylbutyl and 3-methylbutyl groups, which may be substituted by a hydroxyl group at a desired position. The lower alkyl group represented by $R_5$ in Formula (I) is a straight- or branched-chain alkyl group having 1 to 5 carbon atoms, and preferred examples include isobutyl, propyl, methyl and ethyl groups, which may be substituted by one or more groups selected from among hydroxyl, amino and lower alkylamino having 1 to 3 carbon atoms.

The compounds of Formula (I) of the present invention are novel and may be produced by processes which slightly vary according to the starting material used. The processes for producing the compounds of Formula (I) are hereunder described in (A) to (C) as classified by starting material.

(A) Process starting from pregnenolone acetate (3β-hydroxy-5-pregnen-20-one acetate)

Pregnolone acetate is brominated at 7-position by reaction with N-bromosuccinimide under reflux conditions in carbon tetrachloride in the presence of sodium hydrogencarbonate. The acetate is then dehydrobrominated by reaction with collidine in xylene. The resultant 5,7-diene compound is hydrolyzed with potassium hydroxide in methanol to provide 3β-hydroxy-5,7-pregnadien-20-one (compound 1). The end compound of the present invention is produced by one of the following two methods starting from the compound 1.

In the first method, the compound 1 is subjected to customary techniques for producing the vitamin D skeleton that consist of exposure to ultraviolet radiation in an inert solvent followed by heating in a solvent. By these procedures, 3β-hydroxy-9,10-seco-5,7,10(19)-pregnatrien -20-one (compound 2) is obtained. This compound 2 may be treated by the method of Deluca et al. (see Unexamined Published Japanese Patent Application Nos. 135855/1983, 135856/1983 and 135857/1983) to introduce a hydroxyl group at 1α-position, whereby 1α,3β-dihydroxy-9,10-seco-5,7,10(19)-pregnatrien-20-one (compound 3) is obtained. The compound 3 may be reacted with hydroxylamine hydrochloride in pyridine to obtain 20-hydroxyimino-9,10-seco-5,7,10(19)-pregnatriene-1α,3β-diol (compound 4). Compounds 2,3 and 4 obtained by these procedures are within the scope of the present invention.

In the second method, compound 1 is reacted with dihydropyran in the presence of an acid catalyst to introduce tetrahydropyranyl ether at 3-position, and the resulting compound is reacted with hydroxylamine hydrochloride in pyridine to form 20-hyroxyimino-3β-(2-tetrahydropyranyloxy)- 5,7-pregnadiene (compound 5). Alternatively, a hydroxyimino group is directly introduced into the compound 1 at 20-position without protecting the hydroxyl group at 3-position, whereby 20-hydroxyimino-5,7-pregnadien-3β-ol (compound 6) is obtained. Compounds 5 and 6 are reacted with an alkylating agent of the formula R'₅-Z (where R'₅ is the same as R₅ except for a hydrogen atom; and Z is a halogen atom or an electron attractive group such as p-tosyloxy) in the presence of a base, so as to obtain a 20-alkyloxyimino-5,7-pregnadien-3β-ol of Formula (II) corresponding to compound 5 or 6:

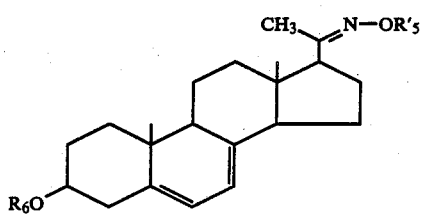

where R'₅ is the same as defined above; and R₆ is a hydrogen atom or 2-tetrahydropyranyl group. The alkylating agent of the formula R'₅-Z may be replaced by an alkyloxirane compound of Formula (III):

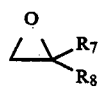

where R₇ and R₈ are each a hydrogen atom or a lower -alkyl group. In this modified case of alkylation, the oxime (i.e., compound 5 or 6) is converted to an oxyiminoanion by a base and the resulting anion will attack the oxirane ring. If, for example, compound 5 is alkylated with an alkyloxirane of Formula (III) where both R and R are a methyl group, 20-(2-hydroxy-2-methylpropyl)oxyimino-3β-(2-tetrahydropyranyloxy)-5,7-pregnadiene (compound 7) is obtained.

If, on the other hand, compound 5 is reacted with epibromohydrin as an alkylating agent of the formula R'₅-Z, a compound of Formula (II) wherein R'₅ is a 2,3-epoxypropyl group and R₆ is a 2-tetrahydropyranyl group is obtained. This compound is then reacted either with a lower alkylamine to form a compound of Formula (II-2), or with a lower alcohol in the presence of an acid catalyst to form a compound of Formula (II-b):

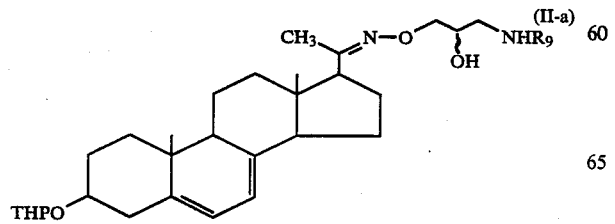

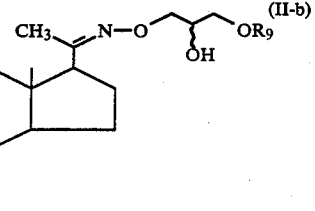

where R₉ is a lower alkyl group; and THP is a 2-tetrahydropyranyl group.

The compound of Formula (II) thus prepared [including the compounds of Formulas (II-a) and (II-b)] is exposed to ultraviolet radiation from a high-pressure mercury lamp under cooling in an inert solvent and an argon atmosphere, whereby the corresponding previtamin D derivative is formed. This previtamin D derivative is further heated to produce a 20-alkyloxyimino-9,10-seco-5,7,10(19)-pregnatrien-3β-ol of Formula (I) where R₅ is a substituted or unsubstituted lower alkyl group. If the compound of Formula (II) is such that R₆ is protected by 2-tetrahydropyranyl group, said protective group is preferably eliminated before the compound is subjected to the sequence of exposure to ultraviolet radiation and thermal isomerization.

If the 20-hydroxyimino (compound 4) obtained by the first method is treated by the alkylation method described in connection with the second method, or if the 20-keto compound (compound 3) is directly reacted with a lower alkyloxyamine typified by methoxyamine or ethoxyamine, 20-alkyloxyimino-9,10-seco-5,7,10(19)-pregnatriene-1α,3β-diol of Formula (I) where R₁ is a hydroxyl group and R₅ is a substituted or unsubstituted lower alkyl group may be obtained. The end compound of the present invention may also be obtained by carrying out the reactions described above, with the hydroxyl group at 1α- or 3β-position being protected by a suitable group.

(B) Process starting from pregnenolone:

Pregnenolone is treated by the method of Dyges et al. [see J.O.C., 44, 1590 (1979)] to form an ether compound of the following formula:

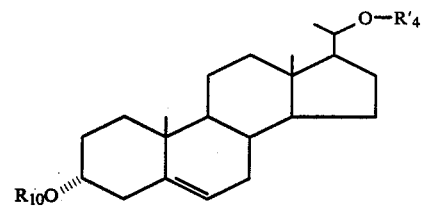

where R₁₀ is a tri-loweralkylsilyl group such as a triethylsilyl group or tert-butyldimethylsilyl group; and R'₄ is the same as R₄ except that it does not include a hydrogen atom. The protective group for the hydroxyl group at 3β-position is so converted as to make 3β-acetoxy-20-(3-loweralkyloxy)-5-pregnene, which is then subjected to bromination at 7-position and dehydrobromination. The resulting provitamin D form is treated by customary techniques to obtain a vitamin D derivative of the following formula which is included within the scope of the end compound of the present invention.

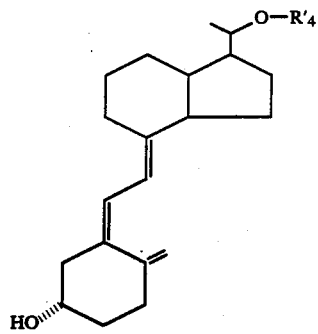

(C) Process starting from dehydroepiandrosterone

Dehydroepiandrosterone is microbially converted to 1α-hydroxy-dehydroepiandrosterone. The hydroxyl group at 1α- and 3β-positions is converted to a tri-loweralkylsilyl group to prepare a compound of Formula (IV):

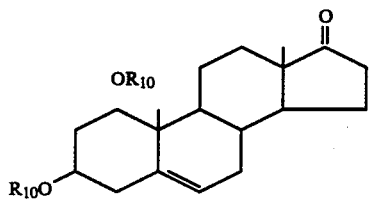

$R_{10}$ is a tri-loweralkylsilyl group such as triethylsilyl or tert-butyldimethylsilyl. This starting compound is subjected to either one of the following procedures (C-1), (C-2) and (C-3).

(C-1): The compound of Formula (IV) is subjected to the Witting reaction using ethyltriphenyl phosphonium bromide, and the resulting ethyldiene compound of Formula (V) is treated by the following scheme:

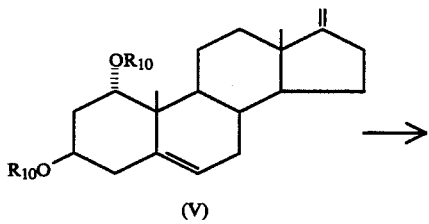

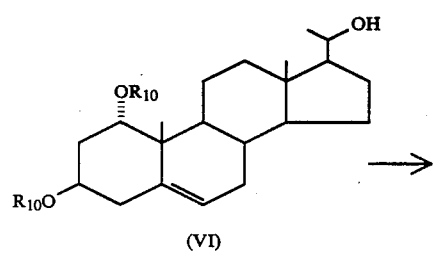

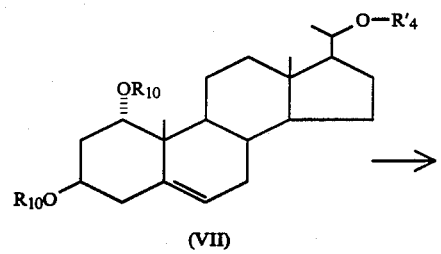

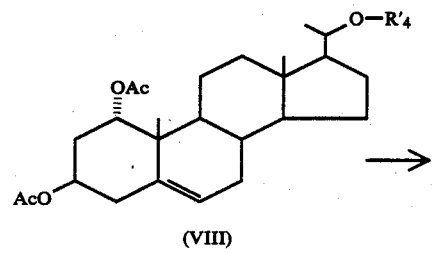

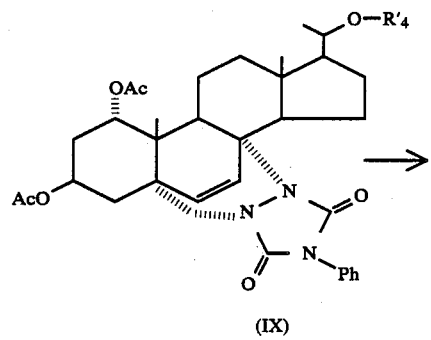

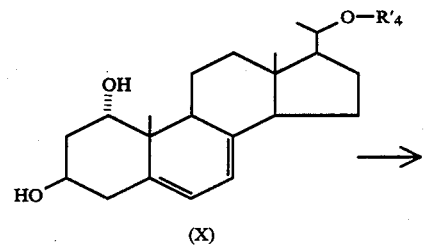

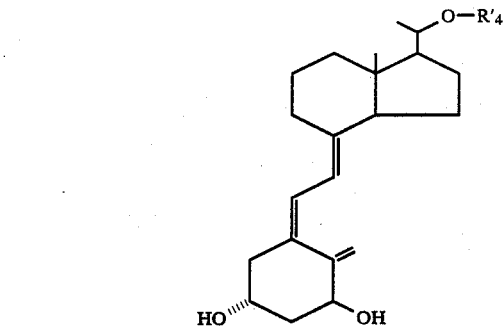

where $R_{10}$ and $R'_4$ are each the same as defined above; and Ph is a phenyl group.

Compound (VI) may be obtained by subjecting compound (V) to hydroboration using 9-borabicyclo [3,3,1] noname. The compound (VI) is then alkylated with a lower alkyl bromide of the formula $R'_4$-Br to form an ether compound (VII). The protective group for the hydroxyl group in the compound (VII) is routinely converted to provide a diacetate compound (VIII). The compound (VIII) is converted to a provitamin D compound (X) by the methods shown in Unexamined Published Japanese Patent Application Nos. 19752/1976 and 84555/1975 that comprise halogenation at 7-position and dehydrohalogenation, followed by addition of 4-phenyl-1,2,4-triazoline-3,5-dione and reduction with lithium aluminum hydride. The provitamin $D_3$ compound (X) is subjected to a sequence of exposures to UV radiation and thermal isomerization to produce a compound (XI) which is included within the scope of the present invention.

(C-2): A compound of Formula (IV) where $R_{10}$ is a tertbutyldimethylsilyl group is subjected to bromination at 7-position and dehydrobromination. The resulting $1\alpha,3\beta$-bis(tert-butyldimethylsilyloxy)-5,7-androstadien-17-one (compound 8) is subjected to the Witting reaction as in the case of conversion to compound (V) from (IV) in the process (C-1). The resulting ethylidene compound (compound 9) is used as the starting material and subjected to the following reactions:

where Y is a tert-butyldimethylsilyl group; and $R'_4$ is the same as defined above.

In this reaction scheme, compound (1) is obtained by subjecting compound (9) to hydroboration. The compound (10) is directly subjected to exposure to UV radiation and thermal isomerization, followed by elimination of the hydroxyl-protecting group with tetrabutylammonuim fluoride or trifluoroacetic acid, whereby a vitamin D derivative (compound 11) that is included with in the scope of the present invention is obtained. The compound (10) may be reacted with a lower alkyl bromide of the formula $R'_4$-Br to form a compound (XII). A compound (XIII) may be obtained by subjecting the compound (XII) to the same reactions as employed to produce compound (11) from compound (10). (C-3): Compound 8 described in connection with the process (C-2) is subjected to the method of Neef et al. [see Chem. Ber., 113, 1184 (1980)] and the resulting $1\alpha,3\beta$-bis(tert-butyldimethylsilyoxy)-20-methoxy-5,7,17(20)-pregnatriene-21-ol (compound 12) is used as the starting material for either one of the following processes, (i) and (ii):

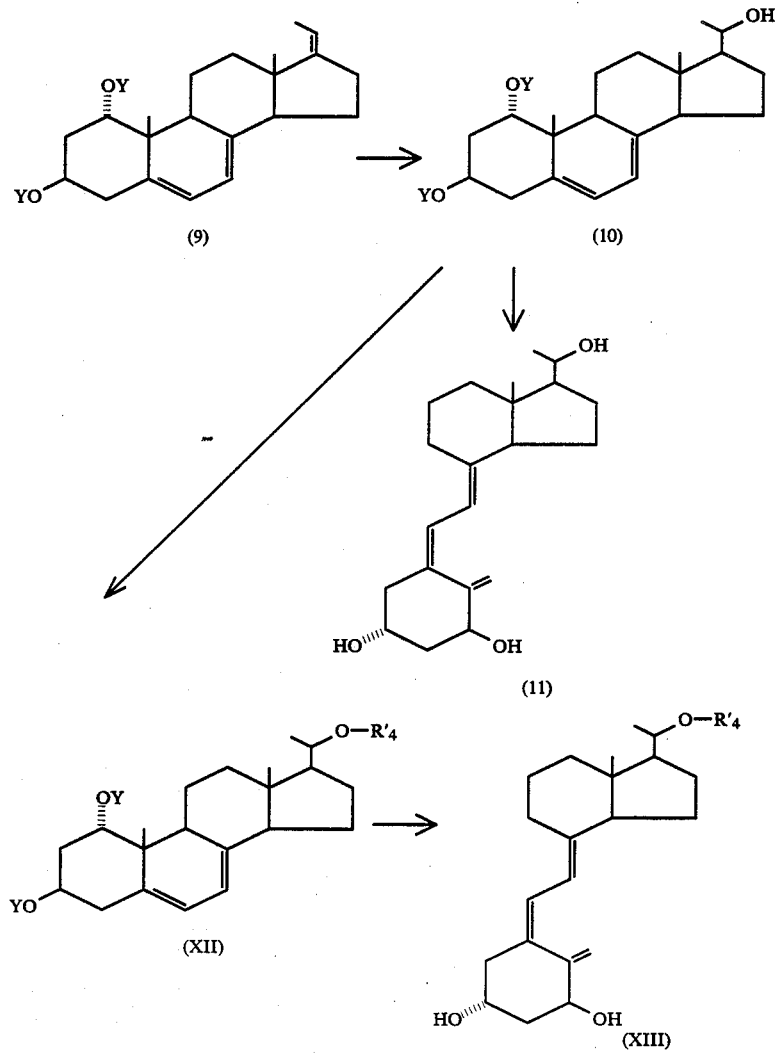

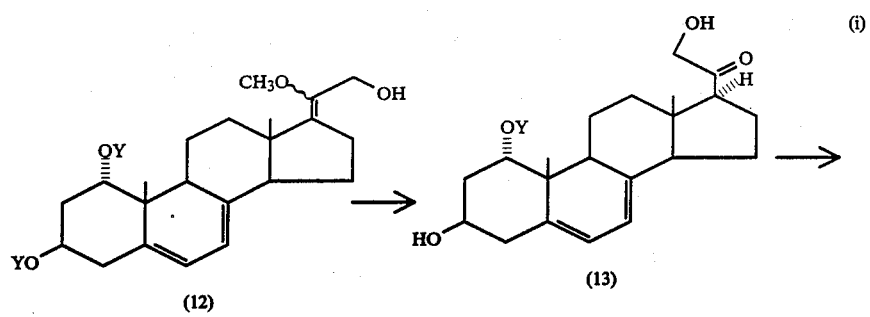
(i)
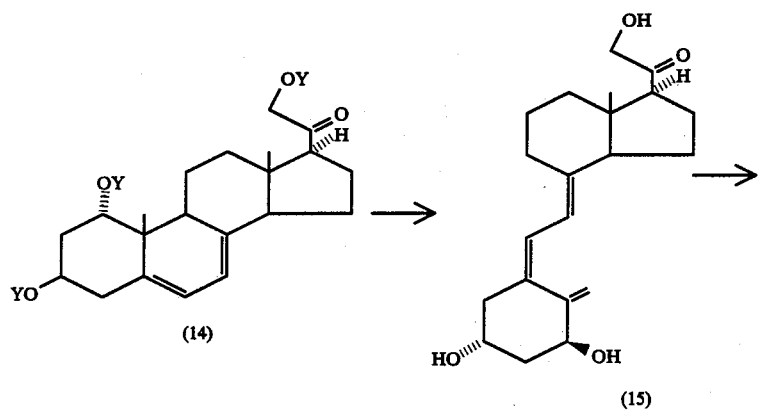
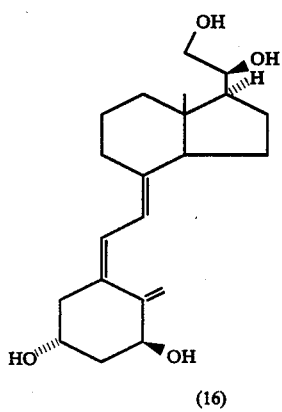
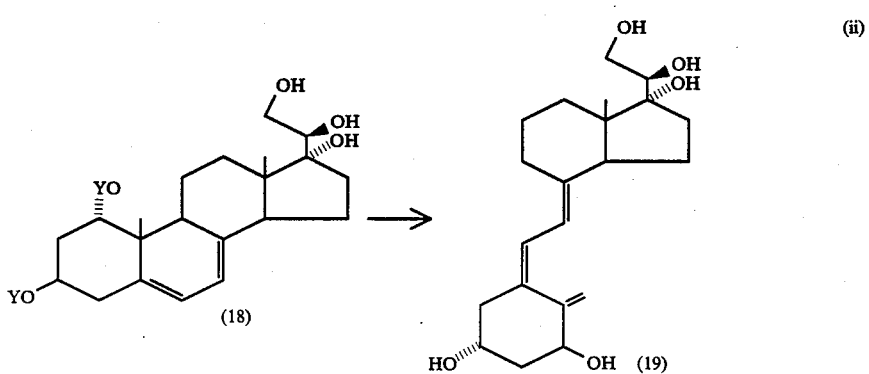
(ii)

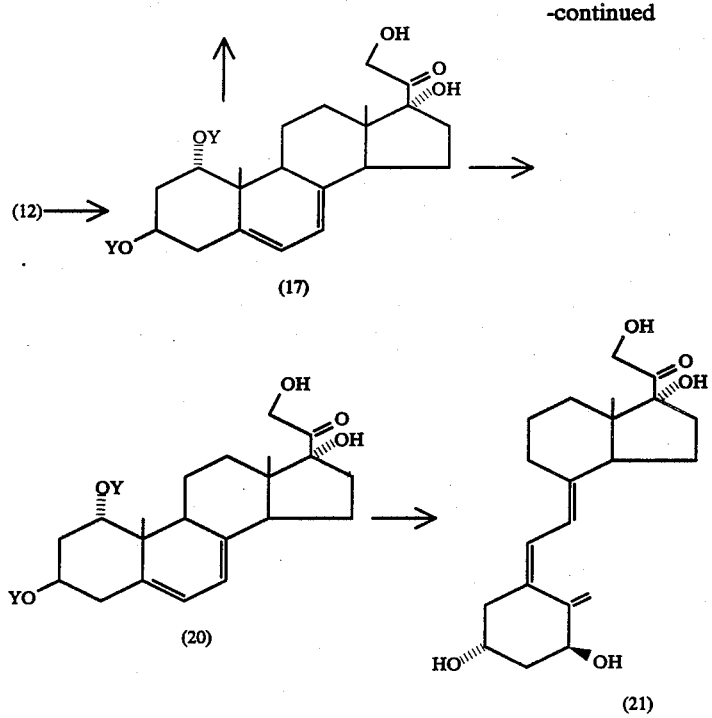

where Y is the same as defined above.

In the scheme (i), compound 13 may be prepared from compound 12 by treating it with oxalic acid in accordance with the method of Neef et al. [Chem. Ber., 113; 1184 (b 1980)]. The resulting compound 13 is reacted with tert-butyldimethyl-silyl chlorine is the presence of a base to form compound 14 where the hydroxyl group at 1α- and 21-positions is protected. Compound 15 which is within the scope of the present invention may be obtained by subjecting the compound 14 to the same reaction as is employed for converting compound 10 to compound 11 in the process (C-2). By subjecting the compound 15 to reduction with sodium borohydride, compound 16 which is also within the scope of the present invention may be produced.

In the scheme (ii), compound 17 may be prepared by treating compound 12 with m-chloroperbenzoic acid. Reduction of compound 17 to compound 18, conversion of compound 18 to compound 19, conversion of compound 20 to compound 21, and preparation of compound 20 from compound 17 by protecting the hydroxyl group at 21-position may be carried out by the same procedures as employed in the scheme (i) described above.

Pharmacological Effects

The differentiation inducing ability and the immunoregulating action of the compounds of Formula (I) were confirmed by the NBT reduction test using HL-60 cells, the anti-SRBC PFC assay and the anti-DNP-Ficoll PFC assay described in the following pages. Experimental data for the effects of the compounds on calcium metabolism are also described below.

(1) NBT reduction test

A flat-bottomed microplate with 96 holes was inoculated with HL-60 cells (human promyelocytic leukemia cell line) which were cultured for 3–4 days together with selected compounds of the present invention. The cultured cells were precipitated by centrifugation and, after removing the supernatant, the cells were resuspended in an RPMI-1640 medium that contained NBT (nitro blue tetrazolium, 1 mg/ml) and TPA (12-O-tetradecanoylphorbol-13-acetate, 100 ng/ml) and which was added into each of the holes in an amount of 100 μl. After leaving the microplate in a $CO_2$ incubator (37° C.) for 20 minutes, all the cells were dropped to the bottom by centrifugation. Under observation with an inverted microscope, the total number of cells within a given visual field and the number of NBT reduction positive cells (those which were stained blue with the water-insoluble formazan that formed upon reduction of the pale yellow NBT) were counted. The differentiation inducing ability of the test compounds was determined in terms of (number of NBT reduction positive cells/total cell number) x 100. The NBT-reduced activity is a marker of the normal macrophage. The results are shown in Table 1, wherein the number assigned to the compounds of the present invention correspond to the numbers of the Examples to be shown later in this specification. This also applies to Tables 2 to 19.

TABLE 1

| Compound No. | Dose (M) | Percentage of the number of NBT reduction positive cells (mean ± S.D.) |
|---|---|---|
| control | — | <3% |
| 1α,25-dihydroxy vitamin $D_3$ | $10^{-9}$ | 9.2 ± 0.7 |
|  | $10^{-8}$ | 82.4 ± 4.2 |
| 2 | $10^{-6}$ | 74.6 ± 3.6 |
|  | $3 \times 10^{-6}$ | >95 |
| 9 | $10^{-7}$ | >95 |
| 11 | $10^{-5}$ | >90 |
| 12 | $10^{-5}$ | >90 |
| 15 | $10^{-6}$ | >90 |
|  | $10^{-6}$ | 22.1 ± 6.6 |
| 16 | $10^{-5}$ | 87.8 ± 1.5 |
|  | $10^{-9}$ | 64.1 ± 4.2 |
| 17 | $10^{-8}$ | >95 |

(2) Anti-SRBC PFC assay

Immunization schedule

BALB/C mice in groups each consisting of 5–6 heads were immunized by intraperitoneal administration of SRBC (sheep red blood cells) in a suboptimal concentration (0.2%/0.2 ml/head). Selected compounds of the present invention dissolved in middle-chain triglyeride (MCT) were administered orally to the mice both immediately after the primary sensitization and 24 hours later.

Assay (i) Preparation of target cells: Thoroughly washed SRBC were added into medium in a concentration of 40%.

(ii) PFC assay:

Each of the treated mice was bled and spleen cells were extracted. A single cell suspension was prepared for counting the total number of spleen cells. A complement was prepared by diluting two-fold a dried complement available from Denka Seiken. An intimate mixture of 40% SRBC (25 µl), the complement (25 µl), and the spleen cell suspension (200 µl) was prepared and 100 µl thereof was put into a Cunningham chamber, where it was incubated at 37° C. for 1 hour, followed by PFC counting.

(iii) Results:

The total number of spleen cells, the PFC count for the total number of spleen cells and the PFC count for a given number of spleen cells were calculated and the results are shown in Tables 2 to 8.

TABLE 2

|  | MCT only | Compound No. 6 | |
| --- | --- | --- | --- |
| Dose (µg/Kg) | — | 0.01 | 0.1 |
| Number of animals | 6 | 6 | 6 |
| Total number of spleen cells (× 10⁷) | 17.4 ± 0.9 | (a) 14.9 ± 0.6 | 18.2 ± 0.8 |
| PFC/Spleen | 2887 ± 265 | (b) 5473 ± 621 | (b) 7200 ± 975 |
| PFC/10⁶ cells | 16.8 ± 1.5 | (b) 37.0 ± 4.2 | (c) 39.2 ± 4.5 |

(a) P <0.1
(b) P <0.01
(c) P <0.001

TABLE 3

|  | MCT only | Compound No. 6 | |
| --- | --- | --- | --- |
| Dose (µg/Kg) | — | 0.01 | 0.1 |
| Number of animals | 6 | 6 | 6 |
| Total number of spleen cells (× 10⁷) | 18.0 ± 0.7 | 17.1 ± 0.7 | 15.2 ± 1.5 |
| PFC/Spleen | 5960 ± 1226 | 6940 ± 640 | (a) 10547 ± 1145 |
| PFC/10⁶ cells | 33.4 ± 6.8 | 40.6 ± 3.2 | (a) 70.6 ± 6.2 |

(a) P <0.05

TABLE 4

|  | MCT only | Compound No. 11 | |
| --- | --- | --- | --- |
| Dose (µg/Kg) | — | 0.1 | 1.0 |
| Number of animals | 6 | 6 | 6 |

TABLE 4-continued

|  | MCT only | Compound No. 11 | |
| --- | --- | --- | --- |
| Total number of spleen cells (× 10⁷) | 19.6 ± 0.7 | 17.3 ± 1.2 | 18.2 ± 1.4 |
| PFC/Spleen | 8958 ± 908 | (c) 15502 ± 940 | (b) 15823 ± 2148 |
| PFC/10⁶ cells | 45.7 ± 4.5 | (c) 90.6 ± 4.6 | (a) 89.6 ± 15.8 |

(a) P <0.025
(b) P <0.01
(c) P <0.0005

TABLE 5

|  | MCT only | Compound No. 12 |
| --- | --- | --- |
| Dose (µg/Kg) | — | 0.05 |
| Number of animals | 6 | 6 |
| Total number of spleen cells (× 10⁷) | 17.55 ± 2.5 | 15.98 ± 4.0 |
| PFC/Spleen | 3940 ± 927 | (a) 5647 ± 1648 |
| PFC/10⁶ cells | 22.27 ± 6.0 | (a) 39.00 ± 19.4 |

(a) P <0.05

TABLE 6

|  | MCT only | Compound No. 13 | |
| --- | --- | --- | --- |
| Dose (µg/Kg) | — | 0.2 | 1.0 |
| Number of animals | 4 | 5 | 6 |
| Total number of spleen cells (× 10⁷) | 19.6 ± 1.8 | 18.1 ± 1.2 | 16.4 ± 0.8 |
| PFC/Spleen | 4860 ± 1236 | 8712 ± 1552 | 5063 ± 890 |
| PFC/10⁶ cells | 23.9 ± 4.2 | (a) 47.9 ± 7.9 | 30.4 ± 4.2 |

(a) P <0.05

TABLE 7

|  | MCT only | Compound No. 14 | |
| --- | --- | --- | --- |
| Dose (µg/Kg) | — | 10.0 | 1.0 |
| Number of animals | 6 | 6 | 6 |
| Total number of spleen cells (× 10⁷) | 9.6 ± 0.7 | 18.1 ± 0.7 | 18.8 ± 1.2 |
| PFC/Spleen | 8958 ± 908 | (b) 16490 ± 1762 | 10646 ± 844 |
| PFC/10⁶ cells | 45.7 ± 4.5 | (c) 90.7 ± 8.1 | (a) 57.2 ± 4.4 |

(a) P <0.05
(b) P <0.005
(c) P <0.0005

TABLE 8

|  | MCT only | Compound No. 15 | |
| --- | --- | --- | --- |
| Dose (µg/Kg) | — | 0.2 | 1.0 |
| Number of animals | 4 | 6 | 6 |
| Total number of spleen cells (× 10⁷) | 19.6 ± 1.8 | (a) 15.9 ± 0.7 | 16.8 ± 0.8 |
| PFC/Spleen | 4860 ± 1236 | (b) 9087 ± 561 | 3110 ± 425 |
| PFC/10⁶ cells |  | (c) |  |

TABLE 8-continued

| MCT only | Compound No. 15 | |
|---|---|---|
| 23.9 ± 4.2 | 55.3 ± 3.1 | 19.1 ± 3.2 |

(a) P <0.1
(b) P <0.01
(c) P <0.001

(3) Anti-DNP-Ficoll PFC assay

Immunization schedule

BALB/C mice in groups each consisting of 5-6 heads were immunized by intraperitoneal administration of DNP-Ficoll in an optimal concentration (10 μg/100 μl/head). Selected compounds of the present invention dissolved in MCT were administered orally to the mice for a period of 5 days starting right after the primary immunization and ending one day before the assay.

Assay (i) Preparation of target cells:

An intimate 1:10:10 mixture of 50% SRBC, 0.75% DNP-BSA (7.5 mg/ml) and 0.5 mM $CrCl_3 \cdot 6H_2O$ was incubated for 1 hour at 37° C. The mixture was washed with saline to make 40% DNP-BSA-SRBC with medium.

(ii) PFC assay:

The treated mice were bled and spleen cells were extracted. A single cell suspension was prepared to count the total number of spleen cells. A complement was prepared by two-fold dilution of a dried complement available from Denka Seiken. An intimate mixture of 40% DNP-BSA-SRBC (25 μl), the complement (25 μl) and the spleen cell suspension (200 μl) was prepared and 100 μl thereof was put into a Cunningham chamber and incubated for 2 hours at 37° C., followed by PFC counting.

(iii) Results:

The total number of spleen cells, the PFC count for the total number of spleen cells and the PFC count for a given number of spleen cells were calculated and the results are shown in Tables 9 to 12.

TABLE 9

| | MCT only | Compound No. 2 | |
|---|---|---|---|
| Dose (μg/Kg) | — | 0.01 | 0.1 |
| Number of animals | 6 | 5 | 6 |
| Total number of spleen cells (× $10^7$) | 13.0 ± 0.8 | 12.6 ± 0.7 | 11.3 ± 0.5 |
| PFC/Spleen | 143300 ± 3800 | (a) 123900 ± 6300 | (a) 120400 ± 7500 |
| PFC/$10^6$ cells | 1124 ± 68 | 990 ± 57 | 1068 ± 63 |

(a) P <0.025

TABLE 10

| | MCT only | Compound No. 6 | |
|---|---|---|---|
| Dose (μg/Kg) | — | 0.01 | 0.1 |
| Number of animals | 6 | 5 | 6 |
| Total number of spleen cells (× $10^7$) | 9.6 ± 0.6 | 10.2 ± 0.4 | 8.9 ± 0.3 |
| PFC/Spleen | 150200 ± 10200 | (a) 87300 ± 5500 | (a) 76600 ± 6300 |
| PFC/$10^6$ cells | | (a) | (a) |

TABLE 10-continued

| MCT only | Compound No. 6 | |
|---|---|---|
| 1577 ± 99 | 857 ± 62 | 868 ± 76 |

(a) P <0.001

TABLE 11

| | MCT only | Compound No. 11 | |
|---|---|---|---|
| Dose (μg/Kg) | — | 0.01 | 0.1 |
| Number of animals | 6 | 6 | 6 |
| Total number of spleen cells (× $10^7$) | 14.1 ± 0.6 | 14.5 ± 0.5 | 13.8 ± 0.9 |
| PFC/Spleen | 141700 ± 10900 | (b) 99600 ± 9800 | (c) 90000 ± 5500 |
| PFC/$10^6$ cells | 1023 ± 116 | (a) 686 ± 63 | (b) 662 ± 52 |

(a) P <0.025
(b) P <0.01
(c) P <0.005

TABLE 12

| | MCT only | Compound No. 15 | |
|---|---|---|---|
| Dose (μg/Kg) | — | 1.0 | 10.0 |
| Number of animals | 5 | 5 | 5 |
| Total number of spleen cells (× $10^7$) | 13.1 ± 0.7 | 11.3 ± 0.8 | 10.5 ± 0.7 |
| PFC/Spleen | 125600 ± 12600 | 127800 ± 11400 | (a) 72400 ± 6400 |
| PFC/$10^6$ cells | 959 ± 75 | 1174 ± 195 | (a) 687 ± 31 |

(a) P <0.005

(4) Effects on calcium metabolism (i) Single administration:

Male weanling Sprague Dawley rats in groups each consisting of 6 heads weighing 45–50 g were fed Diet 11 and deionized water for 3 weeks under an incandescent lamp. Selected compounds of the present invention, and two controls 25-hydroxy vitamin $D_3$ (25-OH-$D_3$) and 1α-hydroxy vitamin $D_3$ (1α-OH-$D_3$) were dissolved in ethanol and administered intravenously to the rats. The treated rats were starved for 24 hours and blood samples were taken from each animal by cardiac puncture. Plasma was isolated from each blood sample and the contents of calcium and inorganic phosphorus in the plasma were measured by the OCPC method described in Am. J. Clin. Path., 45, 290 (1966) and Biochem. J., 65, 709 (1957).

(ii) Continuous administration for 5 days:

Rats of the same species as used in (i) that were in groups of 6 heads were fed as in (i). To these animals, selected compounds of the present invention and control vitamin $D_3$ compounds as dissolved in MCT were administered orally for 5 consecutive days. After application of the final dose, the animals were starved for 24 hours and blood samples were taken from each animal by cardiac puncture. The contents of calcium and inorganic phosphorus in the collected samples were determined by the same method as used in (i).

(iii) Results:

The effects of the test compounds on calcium metabolism as determined in (i) and (ii) are shown in Tables 13 to 19. Tables 13 to 17 show the results of single administration (i.v.), whereas Tables 18 and 19 show the results of both single administration and continuous administration (p.o.).

TABLE 13

(i.v.)

| | Dose | plasma calcium (Mean ± S.D.) mg/dl | plasma inorganic phosphrous (Mean ± S.D.) mg/dl |
|---|---|---|---|
| Control EtOH | 0.5 ml/Kg | 4.598 ± 0.235 | 6.956 ± 1.024 |
| Compound No. 11 | 12.5 μg/0.5 ml/kg | 4.977 ± 0.147 (a) | 6.663 ± 0.700 |
| | 125 μg/0.5 ml/kg | 5.128 ± 0.324 (a) | 6.742 ± 0.797 |
| 1α-OH—D₃ | 6.25 μg/0.5 ml/kg | 6.125 ± 0.198 (b) | 6.102 ± 0.468 |
| 25-OH—D₃ | 6.25 μg/0.5 ml/kg | 6.468 ± 0.258 (b) | 6.047 ± 0.506 |

(a) $P < 0.05$
(b) $P < 0.001$

TABLE 14

(i.v.)

| | Dose | plasma calcium (Mean ± S.D.) mg/dl | plasma inorganic phosphrous (Mean ± S.D.) mg/dl |
|---|---|---|---|
| Control EtOH | 0.5 ml/kg | 5.057 ± 0.543 | 7.537 ± 0.768 |
| Compound No. 14 | 12.5 μg/0.5 ml/kg | 5.517 ± 0.288 | 7.605 ± 0.878 |
| | 125 μg/0.5 ml/kg | 5.633 ± 0.376 (a) | 7.497 ± 0.493 |
| 1α-OH—D₃ | 6.25 μg/0.5 ml/kg | 7.095 ± 0.479 (a) | 7.893 ± 0.603 |
| 25-OH—D₃ | 6.25 μg/0.5 ml/kg | 6.778 ± 0.473 | 7.753 ± 0.735 |

(a) $P < 0.001$

TABLE 15

(i.v.)

| | Dose | plasma calcium (Mean ± S.D.) mg/dl | Plasma inorganic phosphrous (Mean ± S.D.) mg/dl |
|---|---|---|---|
| Control EtOH | 0.5 ml/kg | 5.242 ± 0.653 | 8.292 ± 1.824 |
| Compound No. 15 | 12.5 μg/0.5 ml/kg | 5.035 ± 0.506 | 8.227 ± 1.046 |
| | 125 μg/0.5 ml/kg | 5.147 ± 0.528 (a) | 7.767 ± 1.392 (a) |
| 1α-OH—D₃ | 6.25 μg/0.5 ml/kg | 7.037 ± 1.282 (a) | 6.192 ± 0.607 |
| 25-OH—D₃ | 6.25 μg/0.5 ml/kg | 5.928 ± 0.240 | 7.852 ± 0.738 |

(a) $P < 0.05$

TABLE 16

(i.v.)

| | Dose | plasma calcium (Mean ± S.D.) mg/dl | plasma inorganic phosphorous (Mean ± S.D.) mg/dl |
|---|---|---|---|
| Control EtOH | 0.5 ml/kg | 4.933 ± 0.260 | 7.297 ± 0.909 |
| Compound No. 16 | 12.5 μg/0.5 ml/kg | 4.698 ± 0.250 (a) | 7.095 ± 0.531 |
| | 125 μg/0.5 ml/kg | 4.552 ± 0.280 (b) | 7.485 ± 1.009 |
| 1α-OH—D₃ | 6.25 μg/0.5 ml/kg | 5.990 ± 0.458 (b) | 6.837 ± 0.615 |

TABLE 16-continued (i.v.)

| | Dose | plasma calcium (Mean ± S.D.) mg/dl | plasma inorganic phosphorous (Mean ± S.D.) mg/dl |
|---|---|---|---|
| 25-OH—D₃ | 6.25 μg/0.5 ml/kg | 6.947 ± 0.549 | 7.102 ± 0.623 |

(a) $P < 0.05$
(b) $P < 0.001$

TABLE 17

(i.v.)

| | Dose | Plasma calcium (Mean ± S.D.) mg/dl | Plasma inorganic phosphorous (Mean ± S.D.) mg/dl |
|---|---|---|---|
| Control EtOH | 0.5 ml/kg | 5.092 ± 0.222 | 9.112 ± 0.884 |
| Compound No. 17 | 12.5 μg/0.5 ml/kg | 4.535 ± 0.214 (a) | 7.815 ± 0.595 (b) |
| | 125 μg/0.5 ml/kg | 4.947 ± 0.404 (c) | 8.790 ± 0.562 |
| 1α-OH—D₃ | 6.25 μg/0.5 ml/kg | 6.353 ± 0.334 (c) | 8.228 ± 1.525 (b) |
| 25-OH—D₃ | 6.25 μg/0.5 ml/kg | 6.542 ± 0.285 | 7.397 ± 1.274 |

(a) $P < 0.01$
(b) $P < 0.05$
(c) $P < 0.001$

TABLE 18

| | | plasma calcium (Mean ± S.D.) mg/dl | |
|---|---|---|---|
| | Dose | single administration (i.v.) | continuous administration (p.o.) |
| Control | — | 4.788 ± 0.181 | 5.158 ± 0.230 |
| Compound No. 2 | 12.5 μg/0.5 ml/kg | 4.613 ± 0.327 (a) | 5.014 ± 0.182 |
| | 125 μg/0.5 ml/kg | 4.500 ± 0.114 (c) | 4.902 ± 0.226 (a) |
| 25-OH—D₃ | 2.5 μg/0.5 ml/kg | 5.800 ± 0.300 (c) | 5.596 ± 0.279 (b) |
| | 12.5 μg/0.5 ml/kg | 6.196 ± 0.356 | 5.971 ± 0.410 |

(a) $P < 0.05$
(b) $P < 0.01$
(c) $P < 0.001$

TABLE 19

| | | plasma calcium (Mean ± S.D.) mg/dl | |
|---|---|---|---|
| | Dose | single administration (i.v.) | continuous administration (p.o.) |
| Control | — | 5.192 ± 0.193 | 4.620 ± 0.195 |
| Compound No. 4 | 12.5 μg/0.5 ml/kg | 5.147 ± 0.225 (a) | 4.956 ± 0.587 |
| | 125 μg/0.5 ml/kg | 4.903 ± 0.146 (b) | 4.713 ± 0.185 (a) |
| 25-OH—D₃ | 2.5 μg/0.5 ml/kg | 6.010 ± 0.270 (b) | 5.220 ± 0.484 (b) |
| | 12.5 μg/0.5 ml/kg | 6.390 ± 0.330 | 6.567 ± 0.563 |

(a) $P < 0.05$
(b) $P < 0.001$

EXAMPLE 1

(a) Preparation of 3β-hydroxy-5,7-pregnadien-20-one

Pregnenolone acetate (15.0 g) was dissolved in 100 ml of carbon tetrachloride, and after addition of 8.95 g of N-bromosuccinimide and 8 g of a finely powdered sodium bicarbonate, the mixture was refluxed for 30 minutes. After cooling, the reaction mixture was washed with water and dried, followed by the distilling off of the solvent under vacuum. The yellow solid residue was dissolved in 100 ml of xylene and after addition of 4.5 ml of collidine, the solution was refluxed on an oil bath for 1 hour. After cooling, ethyl acetate was added to the solution and the mixture was successively washed with water, dilute hydrochloric acid, water and an aqueous solution of sodium bicarbonate. The washed solution was dried and the solvent was distilled off under vacuum. The residue was dissolved in 100 ml of methanol under heating. After cooling, 4 g of potassium hydroxide was added to the solution, which was then stirred for 4 hours at room temperature. The resulting white precipitate was filtered off. After washing with methanol, the filtrate was freed of the solvent by vacuum distillation, whereby 6.46 g of a crude product of the desired 5,7-diene compound was obtained.

UV spectrum $\lambda_{max}^{EtOH}$ (nm): 293, 280, 270, 262 (sh).

(b) Preparation of 20-hydroxyimino-5,7-pregnadien-3β-ol

The crude 3β-hydroxy-5,7-pregnadien-20-one (1.3 g) prepared in (a) was dissolved in 30 ml of pyridine, and after addition of hydroxylamine hydrochloride (863.2 mg), the solution was stirred for 5 hours at room temperature. After distilling off the pyridine under vacuum, methanol was added to the residue and the precipitating crystal was collected by filtration to obtain 1.04 g of the desired oxime compound.

m.p. 216°–218° C. (recrystallized from ethanol).

(c) Preparation of 20-(2-methylpropyloxyimino)-5,7-pregnadien-3β-ol

A portion (152.2 mg) of the 20-hydroxyimino-5,7-pregnadien-3β-ol obtained in (b) was dissolved in 10 ml of dry dimethylformamide, and after addition of 50 mg of sodium hydride (60% in oil), the mixture was heated to 40°–50° C. and stirred at room temperature for 30 minutes. To the mixture, 0.2 ml of isobutyl bromide was added and the resulting mixture was stirred overnight at room temperature. Ether was added to the stirred mixture, and the organic layer was washed and dried, followed by the distilling off of the solvent under vacuum. The residue was subjected to silica gel column chromatography and eluted with chloroform. The desired fractions were collected and the solvent was distilled off under vacuum to produce 102.4 mg of the desired oxime compound (as needles).

m.p. 148°–150° C. (recrystallized from methanol)
NMR δ(CDCl$_3$): 0.60, 0.86 (each 3H,s), 0.97 (6H,s), 1.82 (3H,s), 3.20–3.90 (1H,m), 5.47 (2H,q,J=5 Hz).

(d) Preparation of 20-(2-methylpropyloxyimino)-9,10-seco-5,7,10(19)-pregnatrien-3β-ol The 20-(2-methylpropyloxyimino)-5,7-pregnadien-3β-ol (102.4 g) obtained in (c) was dissolved in 400 ml of ethanol of guaranteed quality. While an argon gas was bubbled through, the solution was irradiated under a 400 W high-pressure mercury lamp for 7 minutes with ice-cooling. The solvent was distilled off under vacuum and the residue was dissolved in 5 ml of anhydrous tetrahydrofuran (peroxide-free) and the solution was refluxed for 1 hour. After cooling, the solvent was distilled off under vacuum and the residual oil was subjected to column chromatography using Sephadex LH-20 (Pharmacia Fine Chemicals) and eluted with a 65:35 mixed solvent of chloroform and hexane. The desired fractions were collected and the solvent was distilled off under vacuum to obtain 26.8 mg of the end compound as an oil.

UV spectrum $\lambda_{max}^{EtOH}$ (nm): 264.
Mass spectrum (m/e): 385 (M+).

EXAMPLE 2

(a) Preparation of 20-hydroxyimino-3β-(2-tetrahydropyranyloxy)-5,7-pregnadiene

Two grams of the crude 3β-hydroxy-5,7-pregnadien-20-one obtained in Example, 1(a) was suspended in 50 ml of dry dioxane, and after addition of 1 ml of dihydropyran and 0.1 g of p-toluenesulfonic acid, the suspension was stirred for 3 hours at room temperature. Chloroform was added to the yellow clear reaction mixture, which was then washed with an aqueous solution of sodium bicarbonate. The mixture was washed with water and dried, and the solvent was distilled off under vacuum. The residue was dissolved in 5 ml of pyridine, and after addition of 1.33 g of hydroxylamine hydrochloride, the mixture was stirred for 3 hours at room temperature. Chloroform was added to the reaction mixture and the organic layer was washed with water and dried. The residue left after distilling off the solvent under vacuum was subjected to silica gel column chromatography and eluted with chloroform to obtain 1.17 g of the desired oxime compound as a pale yellow solid.

NMRδ(CDCl$_3$): 0.59, 0.95 (each 3H,s), 4.78 (1H,m), 5.33, 5.53 (each 1H,d,J=6 Hz).

(b) Preparation of 20-(2-hydroxy-2-methylpropyloxyimino)5,7-pregnadien-3β-ol

A portion (606 mg) of the 20-hydroxyimino-3β-(2-tetrahydropyranyloxy)-5,7-pregnadiene obtained in (a) was dissolved in 10 ml of dry dimethylformamide, and after addition of 100 mg of sodium hydride (60% in oil), the solution was vigorously stirred for 30 minutes at room temperature. After addition of 0.5 ml of isobutylene oxide, the mixture was heated on an oil bath (80°–100° C.) for 1 hour. After cooling, diethyl ether was added, and the mixture was washed with water and dried, followed by the distilling off of the solvent under vacuum. The residue was subjected to silica gel column chromatography to obtain 271 mg of 20-(2-hydroxy-2-methylpropyloxyimino)-3β-(2-tetrahydropyranyloxy)-5,7pregnadiene.

NMRδ(CDCl$_3$): 0.58, 0.92 (each 3H,s), 1.22 (6H,d, J=5 Hz), 1.86 (3H,s), 4.70 (1H,m), 5.20–5.80 (2H,m).

The oximether obtained above (271 mg) was dissolved in 30 ml of methanol and after addition of 1 g of Amberlist (product of Rhom and Haas), the mixture was stirred for 1 hour at room temperature. After filtering off the Amberlist and washing with methanol, the filtrate and the washings were combined and the solvent was removed by a rotary evaporator. The residue was subjected to silica gel column chromatography and eluted with chloroform containing 5% methanol, whereby 111.4 mg of the desired oxime compound was obtained.

m.p. 187°–189° C. (recrystallized from methanol).
UV spectrum $\lambda_{max}^{EtOH}$ (nm) 294, 282, 270, 262, 253 (sh).

(c) Preparation of 20-(2-hydroxy-2-methylpropyloxyimino)-9,10-seco-5,7,10(19)-pregnatrien-3β-ol The 20-(2-hydroxy-2-methylpropyloxyimino)-5,7-pregnatrien-3β-ol (111.4 mg) obtained in (b) was dissolved in 400 ml of ethanol of guaranteed quality. While being bubbled through with an argon gas, the ice-cooled solution was irradiated with a 400 W high-pressure mercury lamp for 7 minutes. After distilling off the solvent under vacuum, the residue was dissolved in 5 ml of anhydrous tetrahydrofuran (peroxide-free), and the solution was refluxed for 1 hour. After cooling, the solvent was distilled off under vacuum, and the residue was subjected to silica gel column chromatography eluting with chloroform containing 3% acetone. The fractions containing the pure end compound were collected and the solvent was distilled off under vacuum to produce 11.4 mg of the desired vitamin D derivative as an oil.

UV spectrum $\lambda_{max}^{EtOH}$ (nm) 263, 213.
Mass spectrum (m/e): 401 (M+)

EXAMPLE 3

Preparation of 20-hydroxyimino-9,10-seco-5,7,10(19)-pregnatrien-3β-ol

The 20-hydroxyimino-5,7-pregnadien-3β-ol (118.4 mg) obtained in Example 1(b) was dissolved in 400 ml of ethanol of guaranteed quality. While being bubbled through with an argon gas, the ice-cooled solution was exposed to radiation from a 200 W high-pressure mercury lamp through a Vycor glass filter for 8 minutes. After the irradiation, the solvent was distilled off under vacuum and the residue was dissolved in 10 ml of anhydrous tetrahydrofuran (peroxide-free), followed by refluxing for 1.5 hours. The residue left after distilling off the solvent under vacuum was subjected to column chromatography using Sephadex LH-20 (Pharmacia Fine Chemicals) and eluted with a 65:35 mixed solvent of chloroform and hexane. The desired fractions were collected and the solvent was distilled off under vacuum to obtain 16.3 mg of the end compound.

UV spectrum $\lambda_{max}^{EtOH}$ (nm) 265.
Mass spectrum (m/e): 329 (M+).

EXAMPLE 4

Preparation of 3β-hydroxy-9,10-seco-5,7,10(19)-pregnatrien-20-one

Three hundred milligrams of the 3β-hydroxy-5,7-pregnadien-20-one obtained in Example 1(a) was dissolved in 400 ml of ethanol of guaranteed quality. While being bubbled through with an argon gas, the ice-cooled solution was exposed to radiation from a 400 W high-pressure mercury lamp through a Pyrex glass filter for 60 minutes. After the irradiation, the solvent was distilled off under vacuum and the residue was dissolved in 10 ml of anhydrous tetrahydrofuran (peroxide-free), followed by refluxing for 1 hour. The residue left after distilling off the solvent under vacuum was subjected to silica gel column chromatography and eluted with chloroform containing 5% acetone. The desired fractions were collected and the solvent was distilled off under vacuum to obtain 30 mg of 3β-hydroxy-9,10-seco-b 5,7,10(19)-pregnatrien-20-one.

UV spectrum $\lambda_{max}^{EtOH}$ (nm): 263.

EXAMPLE 5

Preparation of 20-hydroxyimino-9,10-seco-5,7,10(19)-pregnatrien-3β-ol

Thirty milligrams of the 3β-hydroxy-9,10-seco-5,7,10(19)-pregnatrien-20-one obtained in Example 4 was dissolved in 5 ml of pyridine, and after addition of 10.4 mg of hydroxylamine hydrochloride, the solution was stirred for 5 hours at room temperature. The pyridine was distilled off under vacuum and the residue was dissolved in chloroform. The chloroform layer was washed with water and dried, followed by the distilling off of the solvent. The residue was subjected to column chromatography using Sephadex LH-20 and eluted with a 65:35 mixture of chloroform and hexane. The desired fractions were collected and the solvent was distilled off under vacuum to obtain 25 mg of the oxime compound. The physical data of this compound were in agreement with that of the product synthesized in Example 3.

EXAMPLE 6

(a) Preparation of 6ξ-methoxy-3,5-cyclo-9,10-seco-7,10(19)-pregnadien-20-one

The 3β-hydroxy-9,10-seco-5,7,10(19)-pregnatrien-20one (968 mg) obtained in Example 4 was dissolved in 10 ml of pyridine, and to the ice-cooled solution, 882.7 mg of p-toluenesulfonyl chloride was added, and the mixture was left to stand for 36 hours at 5° C. The reaction mixture was poured into a cold aqueous solution of sodium bicarbonate, followed by extraction with ether. The ether layer was washed with water and dried. The solvent was distilled off under vacuum to obtain 1.03 g of 3-tosylate as an oil.

The 3-tosylate was dissolved in 100 ml of methanol, and after adding 5 g of sodium bicarbonate, the solution was refluxed for 6 hours. The residue left after distilling off the solvent under vacuum was subjected to extraction with ether. The ether layer was washed with water and dried. The residue left after distilling off the solvent under vacuum was subjected to silica gel column chromatography and eluted with chloroform, giving 292.4 mg of the desired 3,5-cyclo compound as an oil.

NMR spectrum δ(CDCl$_3$): 0.49 (3H,s), 2.09 (3H,s), 3.22 (3H,s), 4.05 (1H,d,J=10 Hz), 4.70–5.20 (3H,m).

(b) Preparation of 1α,3β-dihydroxy-9,10-seco-5,7,10(19)-pregnatrien-20-one

To 50 ml of dichloromethane, 0.5 ml of t-butyl hydroperoxide (70% aq. sol.) was added, and by vacuum distillation on a bath at 40° C., the volume of the solution was reduced to about 20 ml. Another 50-ml of dichloromethane was added to the residue and the resulting solution was treated likewise. To the resultant solution in dichloromethane, 56 mg of selenium dioxide was added and the mixture was stirred for 30 minutes at room temperature. To the solution was added a solution in 10 ml of dichloromethane of 292.4 mg of 6ξ-methoxy-3,5-cyclo-9,10-seco-7,10(19)-pregnadien-20-one obtained in (a). The mixture was stirred for 30 minutes at room temperature. To the mixture, 5 ml of an aqueous solution of 10% sodium hydroxide was added and the mixture was stirred for 30 minutes at room temperature. After adding ether, the mixture was washed with water, then with an aqueous solution of 5% sodium sulfite. The organic layer was dried and the solvent was distilled off under vacuum. The residue was subjected to silica gel column chromatography and eluted with chloroform containing 10% acetone.

The first fraction to be obtained as an eluate contained a 1-oxo compound, which was purified to 64.1 mg of the 1-oxo compound as an oil.

NMR δ(CDCl$_3$): 0.45 (3H,s), 2.09 (3H,s), 3.25 (3H,s), 3.99 (1H,d,J=9 Hz), 4.98 (1H,d,J=9 Hz), 5.49, 5.91 (each 1H,s).

The second fraction contained the desired 1α-OH compound, or 1α-hydroxy-6ξ-methoxy-3,5-cyclo-9,10-seco-7,10(19)-pregnadien-20-one, which was purified to 60.5 mg of the 1α-OH compound as an oil.

NMR δ(CDCl$_3$): 0.49 (3H,s,18-CH$_3$), 2.09 (3H,s,21-CH$_3$), 3.22 (3H,s,-OCH$_3$), 3.95–4.35 (1H m,1-H), 4.11 (1H,d,J=9 Hz,6-H), 4.99 (1H d,J=9 Hz,7-H), 4.99–5.35 (2H,m,19-H).

The 1α-OH compound (60.5 mg) was dissolved in 1.5 ml of pyridine, and after addition of 0.5 ml of acetic anhydride, the solution was stirred at 55°–60° C. for 2 hours. The cooled solution was poured into a cold aqueous solution of sodium bicarbonate, and the mixture was subjected to extraction with ether. The ether layer was washed with water and dried. By distilling off the solvent, 65 mg of 1α-acetoxy compound was obtained as an oil.

NMR δ(CDCl$_3$): 0.50 (3H,s), 2.05 (3H,s), 2.10 (3H,s), 3.22 (3H,s), 4.06 (1H,d,J=9 Hz), 4.88–5.40 (3H,m).

The 1α-acetoxy compound (65 mg) obtained above was dissolved in 3 ml of dioxane, and after successive addition of water (1 ml) and p-toluenesulfonic acid (10 mg), the solution was stirred for 1 hour at room temperature. After addition of an aqueous solution of sodium bicarbonate, the mixture was subjected to extraction with ether. The ether layer was washed with water and dried. The residue left after distilling off the solvent was subjected to silica gel column chromatography and eluted with a 3:7 mixed solvent of ethyl acetate and hexane. The desired fractions were collected, concentrated and dissolved in 3 ml of ethanol. After addition of 1 ml of an aqueous solution of 10% sodium hydroxide, the mixture was stirred overnight at room temperature. The solvent was distilled off under vacuum and the residue was subjected to extraction with ether. The ether layer was washed with water and dried. The residue left after distilling off the solvent was subjected to column chromatography using Sephadex LH-20 and eluted with a 65:35 mixed solvent of chloroform and hexane, giving 24.9 mg of the desired 1α-OH compound.

UV spectrum $\lambda_{max}^{EtOH}$ (nm) 265, 210.
Mass spectrum (m/e): 330 (M+).

EXAMPLE 7

Preparation of
20-hydroxyimino-9,10-seco-5,7,10(19)-pregnatriene-1α,3β-diol

A portion (11.95 mg) of the 1α,3β-dihydroxy-9,10-seco-5,7,10(19)-pregnatrien-20-one obtained in Example 6 was dissolved in 1 ml of pyridine, and after addition of 50 mg of hydroxylamine hydrochloride, the solution was stirred at room temperature for 3 hours. The solvent was distilled off under vacuum and the residue was subjected to extraction with ether. The organic layer was washed with water and dried, followed by the distilling off of the solvent. The residue was subjected to silica gel column chromatography and eluted with chloroform containing 20% acetone. The desired fractions were collected and the solvent was distilled off under vacuum, giving 9.72 mg of the desired oxime compound as an oil.

UV spectrum $\lambda_{max}^{EtOH}$ (nm): 266, 208.
Mass spectrum (m/e): 345 (M+).

EXAMPLE 8

(a) Preparation of
20-(2,3-epoxypropyloxyimino)-3β-(2tetrahydropyranyloxy)-5,7-pregnadiene A portion (862.5 mg) of the 20-hydroxyimino-3β-(2-tetrahydropyranyloxy)-5,7-pregnadiene obtained in Example 2(a) was dissolved in 10 ml of dry dimethylformamide, and after addition of 150 mg of sodium hydride (60% in oil), the solution was stirred for 30 minutes at room temperature. To the solution, 429.9 mg of epi-bromohydrin was added and the mixture was stirred for 1.5 hours on an oil bath at 80° C. After cooling, ether was added to the mixture, and the organic layer was washed with water and dried. The residual oil obtained by distilling off the solvent was subjected to silica gel column chromatography and eluted with chloroform. The desired fractions were collected and the solvent was distilled off to obtain 727.1 mg of the 2,3-epoxypropyl compound.

NMR δ(CDCl$_3$): 0.59 (3H,s), 0.92 (3H,s), 1.83 (3H,s), 2.50–4.40 (10H,m), 4.68 (1H,b.s.), 5.42 (2H,q, J=6 Hz).

(b) Preparation of
20-{2-ξ-hydroxy-3-(methylamino)propyloxyimino}-5,7-pregnadien-3β-ol A portion (465.6 mg) of the 20-(2,3-epoxypropyloxyimino-3β-(2-tetrahydropyranyloxy)-5,7-pregnadiene obtained in (a) was dissolved in 5 ml of ethanol, and after addition of 1 ml of an aqueous solution of 40% methylamine, the solution was stirred for 5 hours at room temperature. Ether was added to the solution and the ether layer was washed with water and dried. The residue left after distilling off the solvent was dissolved in 20 ml of methanol, and after addition of 0.5 g of p-toluenesulfonic acid, the mixture was stirred for 2 hours at room temperature. After addition of an aqueous solution of 5% sodium bicarbonate, the mixture was subjected to extraction with chloroform. The chloroform layer was washed with water and dried. The residue left after distilling off the solvent under vacuum was subjected to silica gel column chromatography and eluted with chloroform containing 30% methanol. The desired fractions were collected and the solvent was distilled off to obtain 212.6 mg (54.4%) of the compound as a pale yellow solid crystal.

NMR δ(CDCl$_3$): 0.57 (3H,s), 0.94 (3H,s), 1.82 (3H,s) 2.29 (3H,s), 2.94 (2H,t), 3.17–3.77 (3H,m), 3.87–4.47 (3H,m), 5.45 (2H,q,J=6 Hz).

(c) Preparation of
20-{2-ξ-hydroxy-3-(methylamino)propyloxyimino}-9,10-seco-5,7,10(19)-pregnatrien-3β-ol A portion (106.3 mg) of the 20-{2-ξ-hydroxy-3-(methylamino)propyloxyimino}-5,7-pregnadien-3β-ol obtained in (b) was dissolved in 400 ml of ethanol of guaranteed quality. While being bubbled through with an argon gas, the ice-cooled solution was exposed to radiation from a 200 W high-pressure mercury lamp for 18 minutes. After distilling off the solvent under vacuum, the residue was dissolved in anhydrous tetrahydrofuran (peroxide-free) and the solution was refluxed for thermal isomerization. The residue left after distilling off the solvent was subjected to column chromatography using Sephadex LH-20 and eluted with a 65:35 mixed solvent of chloroform and hexane. The desired fractions were collected and the solvent was distilled off to give 14.5 mg of the vitamin D derivative as an oil.

UV spectrum $\lambda_{max}^{EtOH}$ (mn): 265, 207.
Mass spectrum (m/e): 416 (M+).

EXAMPLE 9

Preparation of 20α-(3-methylbutyloxy)-9,10-seco-5,7,10(19)-pregnatriene-1α,3β-diol (a) In 600 ml of pyridine, 9.13 g of 1α-hydroxydehydroepiandrosterone was suspended. Under an argon stream, 100 ml of triethylamine and 39.0 g of triethyl chlorosilane were added to the suspension, and the mixture was stirred for 24 hours at room temperature. After adding 500 ml of water, the solvent was distilled off under vacuum. The residue was subjected to extraction with benzene. The benzene layer was successively washed with an aqueous solution of 0.5N HCl, water, saturated sodium hydrogencarbonate and a saturated aqueous solution of sodium chloride, and dried over magnesium sulfate. The residue obtained by distilling off the solvent under vacuum was subjected to silica gel column chromatography and eluted with chloroform, whereby 9.64 g of 1α,3β-bis(triethylsilyloxy)-5-androsten-17-one was obtained as a pale yellow crystal. Part of the compound was recrystallized from methanol to give colorless needles having a melting point of 99°–100° C.

IR $\nu_{max}$ (cm$^{-1}$): 1740, 1080.
NMR δ: 0.3–1.2 (36H,m), 1.3–2.5 (17H,br).
Mass spectrum (m/e): 400 (M+-HOSiEt$_3$).

(b) In 2 ml of dimethyl sulfoxide was suspended 113 mg of 60% sodium hydride, and under a nitrogen stream, the suspension was stirred for 40 minutes at 80°–85° C. To the water-cooled suspension, a solution in dimethyl sulfoxide (4 ml) of ethyl triphenyl phosphonium bromide (1.04 g) was added, and the mixture was stirred for 5 minutes at the same temperature. To the mixture, a solution in dimethyl sulfoxide (10 ml) and tetrahydrofuran (3 ml) of the ketone compound (294 mg) obtained in (a) was added, and the resultant mixture was stirred for 3.5 hours at 60°–65° C. After addition of 20 ml of water, the mixture was subjected to extraction with ether. The ether layer was successively washed with water and saturated aqueous sodium chloride. After drying over magnesium sulfate, the solvent was distilled off under vacuum and the residue was subjected to column chromatography using activated alumina of 300 mesh eluting with hexane to provide a crude product of 1α,3β-bis(triethylsilyloxy)-5,17(20)-pregnadiene as a colorless oil. The crude product was purified by preparative TLC using silica gel (twice operated with 5:1 mixture of petroleum ether and hexane), whereby 210 mg of colorless needles were obtained. Part of this crystal was recrystallized from methanol to produce colorless needles having a melting point of 81°–82° C.

IR spectrum $\nu_{max}$ (cm$^{-1}$): 1080.
NMR spectrum δ: 0.3–1.2 (36H,m), 1.3–2.5 (17H,br), 1.65 (3H,d,J=7 Hz), 3.7–4.2 (2H,br), 5.0–5.2 (1H,br), 5.3–5.5 (1H,br).
Mass spectrum (m/e): 412 (M+-HOSiEt$_3$).

(c) The ethylidene compound (1.07 g) obtained in (b) was dissolved in 10 ml of tetrahydrofuran. To the solution, 10 ml of 9-BBN (0.5M tetrahydrofuran solution) was added under a nitrogen stream, and the mixture was stirred for 3.5 hours at room temperature. After addition of 2 ml of a 3M aqueous sodium hydroxide solution, the mixture was ice-cooled. Two ml of an aqueous solution of 35% hydrogen peroxide was added to the mixture while the temperature of the rotation was held below 45° C., and the mixture was stirred for 1 hour at room temperature. Ether (20 ml) was added to the reaction mixture and the ether layer was successively washed with water and saturated aqueous sodium chloride. After drying over magnesium sulfate, the solvent was distilled off under vacuum and the resulting residue was purified by silica gel column chromatography (elution with a 20:1 mixture of benzene and ethyl acetate). Two products were obtained: 1α,3β-bis(triethylsilyloxy)-5-pregnen-20β-ol (m.p. ca. 80° C., colorless solid, 30 mg) and 1α,3β-bis(triethylsilyloxy)-5-pregnen-20α-ol (m.p. 146°–146.5° C., colorless grain, 0.87 g).

(20α-form)

IR spectrum $\nu_{max}$ (cm$^{-1}$): 3520, 1080.
NMR spectrum δ: 0.3–1.1 (36H,m), 1.22 (3H,d, J=6 Hz), 1.40 (1H,s), 3.5–4.2 (3H,br), 5.3–5.5 (1H,br).
Mass spectrum (m/e): 430 (M+-HOSiEt$_3$), 298.

(20β-form)

IR spectrum $\nu_{max}$ (cm$^{-1}$): 3350, 1080.
NMR spectrum δ: 0.3–1.1 (36H,m), 1.13 (3H,d, J=6 Hz), 1.40 (1H,s), 3.5–4.2 (3H,br), 5.3–5.5 (1H,br).
Mass spectrum (m/e): 430 (M+-HOSiEt$_3$), 298.

(d) To a suspension of 126 mg (3.15 mmol) of 60% sodium hydride in 7 ml of xylene, a solution in xylene (10 ml) of 20α-form (443 mg) obtained in (c) was added under an argon stream, and the mixture was refluxed for 2 hours. After cooling, a solution in xylene (10 ml) of isoamyl bromide (713 mg) was added and the mixture was refluxed for 21 hours. Water (20 ml) was added and the mixture was subjected to extraction with ether. The ether layer was successively washed with water and saturated aqueous sodium chloride. After drying over magnesium sulfate, the solvent was distilled off under vacuum and the resulting residue was purified by silica gel preparative TLC (solvent: a 1:1 mixture of benzene and hexane) to provide 284 mg of 1α,3β-bis(triethylsilyloxy)-20α-(3-methylbutyloxy)-5-pregnene as a pale yellow powder having a melting point of 78°–82° C.

IR spectrum $\nu_{max}$ (cm$^{-1}$): 1090.
NMR spectrum δ: 0.3–1.1 (42H,m), 1.13 (3H,d,J=6 Hz), 3.30 (2H,t,J=6 Hz), 3.5–4.0 (3H,br), 5.3–5.6 (1H,br).
Mass spectrum (m/e): 500 (M+-HOSiEt$_3$), 368.

(e) To a solution in dimethoxyethane (16 ml) of the ether compound (318 mg) obtained in (d), a mixture of methanol (16 ml) and 1N HCl aqueous solution was added, followed by stirring for 1.75 hours at room temperature. The mixture was diluted with 40 ml of a saturated aqueous solution of sodium chloride and subjected to extraction with ethyl acetate. After drying over magnesium sulfate, the solvent was distilled off under vacuum and the residue was purified by preparative silica gel TLC (solvent: a 10:1 mixture of chloroform and ethanol) to obtain 152 mg of 20α-(3-methylbutyloxy)-5-pregnene-1α,3β-diol as a colorless powder having a melting point of 121°–124° C.

IR spectrum $\nu_{max}$ (cm$^{-1}$): 3375.

NMR spectrum 67: 0.66 (3H,s), 0.87 (6H,d,J=6 Hz), 1.00 (3H,s), 1.13 (3H,d,J=6 Hz), 1.2–2.6 (23H,br), 3.2–4.1 (3H,br), 3.27 (2H,t,J=6 Hz), 5.4–5.6 (1H,br).

Mass spectrum (m/e): 404 (M+), 386.

(f) A portion (149 mg) of the diol compound obtained in (e) was dissolved in 10 ml of pyridine and 5 ml of acetic anhydride, and the resulting solution was stirred for 37 hours at room temperature. After adding 20 ml of water, the solution was subjected to extraction with benzene. The benzene layer was successively washed with 10% aqueous HCl solution, water, a saturated aqueous solution of sodium hydrogencarbonate and saturated aqueous sodium chloride. After drying over magnesium sulfate, the solvent was distilled off under vacuum, and the resulting residue was purified by preparative silica gel TLC (solvent: a 10:1 mixture of benzene and ethyl acetate) to obtain 143 mg of 1α,3β-diacetoxy-20α-(3-methylbutyloxy)-5-pregnene as a colorless oil.

IR spectrum $\nu_{max}$ (cm$^{-1}$): 1735, 1240.

NMR spectrum δ: 0.66 (3H,s), 0.90 (6 H 1.08 (3H,s), 1.13 (3H,d,J=6 Hz), 1.2–2.6 (21H,br), 2.00 (3H,s), 2.05 (3H,s), 3.1–3.8 (1H,br), 3.27 (2H,t,J=6 Hz), 4.6–5.2 (2H,br), 5.4–5.6 (1H,br).

Mass spectrum (m/e): 368 (M+-2xCH$_3$COOH), 71.

(g) To a solution in hexane (7 ml) of the diacetate compound (140 mg) obtained in (f), 96 mg of sodium hydrogencarbonate and 66 mg of N-bromosuccinimide were added, and the mixture was refluxed for 1 hour. After dilution with 30 ml of ethyl acetate, the organic layer was successively washed with an aqueous solution of 4% sodium thiosulfate, water and saturated aqueous sodium chloride. After drying over magnesium sulfate, the solvent was distilled off under vacuum. The resulting residue was dissolved in 7 ml of xylene, and after addition of γ-collidine (0.2 ml), the solution was refluxed for 1 hour. After dilution with 20 ml of benzene, the organic layer was successively washed with water, 10% aqueous HCl solution, water, an aqueous solution of saturated sodium hydrogencarbonate and saturated aqueous sodium chloride. After drying over magnesium sulfate, the solvent was distilled off under vacuum. The residue was dissolved in 7 ml of methylene chloride. To the solution, a solution in methylene chloride (2 ml) of 4-phenyl-1,2,4-triazoline-3,5-dione (50 mg) was added, and the mixture was stirred for 1 hour at room temperature. The residue left after distilling off the solvent under vacuum was purified by preparative silica gel TLC (solvent: a 2:1 mixture of benzene and ethyl acetate) to obtain 104 mg of pale yellow semi-solid form of Diels-Alder adduct of 1α,3β-diacetoxy- 20α-(3-methylbutyloxy)-5,7-pregnadiene and 4-phenyl-1,2,4triazoline-3,5-dione (m.p. 102°–107° C).

IR spectrum $\nu_{max}$ (cm$^{-1}$): 1740, 1690, 1240.

NMR spectrum δ: 0.84 (3H,s), 0.89 (6H,d,J=6 Hz), 1.06 (3H,s), 1.13 (3H,d,J=6 Hz), 1.2–2.8 (17H,br), 2.00 (3H,s), 2.02 (3H,s), 3.0–3.7 (3H,m), 5.0–5.2 (1H,br), 5.6–6.0 (1H,m), 6.26 (1H,d, J=8 Hz), 6.45 (1H,d,J=8 Hz), 7.2–7.6 (5H,m).

Mass spectrum (m/e): 426 (M+),71.

(h) Lithium aluminum hydride (97 mg) was suspended in 3 ml of tetrahydrofuran. To the ice-cooled suspension, a solution in tetrahydrofuran (7 ml) of the Diels-Alder adduct (100 mg) obtained in (g) was added under an argon stream, and the mixture was stirred for 0.5 hour as it was warmed to room temperature. The mixture was then refluxed for 1 hour and combined with a 10% aqueous solution of sodium hydroxide under cooling with ice. The mixture was subjected to extraction with ether and the ether layer was successively washed with water and saturated aqueous sodium chloride. The aqueous layer was further subjected to extraction with methylene chloride and the extract was combined with the previously obtained ether layer. After drying the combined organic layer over magnesium sulfate, the solvent was distilled off under vacuum. The resulting residue was purified by preparative silica gel TLC (solvent: a 10:1 mixture of chloroform and ethanol) to obtain 28 mg of a colorless amorphous 20α-(3-methylbutyloxy)-5,7-pregnadiene-1α,3β-diol having a melting point of about 105° C.

IR spectrum $\nu_{max}$ (cm$^{-1}$): 3350.

NMR spectrum δ: 0.61 (3H,s), 0.89 (6H,d,J=6 Hz), 0.94 (3H,s), 1.17 (3H,d,J=6 Hz), 1.2–2.8 (20H,br), 3.39 (2H,t,J=6 Hz), 3.5–4.2 (3H,m), 5.34 (1H,d, J=6 Hz), 5.69 (1H,d,J=6 Hz).

Mass spectrum (m/e): 402 (M+),71.

UV spectrum $\lambda_{max}$ (nm): 293, 282, 271.

(i) A portion (25.6 mg) of the provitamin D derivative obtained in (h) was dissolved in 400 ml of ethanol. While being bubbled through with argon gas, the ice-cooled solution was irradiated under a 200 W high-pressure mercury lamp for 4.5 minutes. The residue left after distilling off the solvent under vacuum was dissolved in 10 ml of tetrahydrofuran and the solution was refluxed for 1 hour. The solvent was distilled off under vacuum and the resulting residue was purified by column chromatography using 10 g of Sephadex LH-20 (elution with a 13:7 mixture of chloroform and hexane) to provide 2.7 mg of 20α-(3-methylbutyloxy)-9,10-seco-5,7,10(19)-pregnatriene-1α,3β-diol.

Mass spectrum (m/e): 402 (M+), 71.

UV spectrum $\lambda_{max}$ (nm): 262, $\lambda_{min}$ (nm): 227.

$[\alpha]_D^{25}$: +27.0° (C=0.27, ethanol).

EXAMPLE 10

Preparation of 20α-(3-methylbutyloxy)-9,10-seco-5,7,10(19)-pregnatrien-3β-ol (a) The starting material, 3β-(tert-butyldimethylsilyloxy)-20α-(3-methylbutyloxy)-5-pregnene (1.12 g), was treated as in Example (9e) and (f), whereby 0.44 g of 3β-acetoxy-20α-(3-methylbutyloxy)-5-pregnene was obtained.

IR spectrum $\lambda_{max}$ (cm$^{-1}$): 1730, 1250.

NMR spectrum δ: 0.65 (3H,s), 0.89 (6H,d,J=6 Hz), 1.01 (3H,s), 1.14 (3H,d,J=6 Hz), 2.00 (3H,s), 3.0–3.7 (3H,m), 4.3–4.8 (1H,br), 5.2–5.4 (1H,br).

Mass spectrum (m/e): 370 (M$^{30}$ -CH$_3$COOH), 71.

(b) A portion (431 mg) of the acetate compound obtained in (a) was dissolved in 15 ml of hexane. To the solution, 277 mg of sodium hydrogencarbonate and 1.2 mmol of N-bromosuccinimide were added and the mixture was refluxed for 2 hours. After cooling, the mixture was diluted with 20 ml of ethyl acetate, and the organic layer was successively washed with an aqueous solution of 3% sodium thiosulfate, water and saturated aqueous sodium chloride. After drying over magnesium sulfate, the solvent was distilled off under vacuum and the resulting residue was dissolved in 15 ml of xylene. After addition of γ-collidine (0.5 ml), the solution was refluxed for 2 hours. The solution was then diluted with benzene (20 ml) and the organic layer was successively washed with water and saturated aqueous sodium chloride. After drying over magnesium sulfate, the solvent was distilled off under vacuum and the resulting residue was purified by silica gel column chromatography (elution by a 25:1 mixed solvent of benzene and ethyl acetate) to obtain 51 mg of a colorless form of 3β-acetoxy-20α-(3-methylbutyloxy)-5,7-pregnadiene.

NMR spectrum δ: 0.60 (3H,s), 0.89 (6H,d,J=6 Hz), 0.99 (3H,s), 1.17 (3H,d,J=6 Hz), 1.2–2.6 (20H,br), 1.99 (3H,s), 3.0–3.8 (3H,m), 4.4–4.9 (1H,br), 5.2–5.7 (1H,br).

Mass spectrum (m/e): 428 (M+), 71.

(c) The 5,7-diene compound (51 mg) obtained in (b), lithium aluminum hydride (30 mg) and tetrahydrofuran (7 ml) were treated as in Example 9(h) to obtain 41 mg of 20α-(3-methylbutyloxy)-5,7-pregnadien-3β-ol.

IR spectrum λ$_{max}$ (cm$^{-1}$): 3230.

NMR spectrum δ: 0.60 (3H,s), 0.88 (6H,d,J=6 Hz), 0.91 (3H,s), 1.17 (3H,d,J=6 Hz), 1.2–2.6 (21H,br), 3.1–3.9 (4H,m), 5.2–5.7 (2H,m).

Mass spectrum (m/e): 386 (M+), 71.

UV spectrum λ$_{max}$ (nm): 292, 281, 270.

(d) The provitamin D derivative (41.4 mg) obtained in (c), ethanol (400 ml) and tetrahydrofuran (15 ml) were treated as in Example 9(i) to obtain 6.1 mg of 20α-(3-methylbutyloxy)-9,10-seco-5,7,10(19)-pregnatrien-3β-ol.

Mass spectrum (m/e): 386 (M+), 71.

UV spectrum λ$_{max}$ (nm): 261, λ$_{min}$ (nm): 226.

Example 11

Preparation of 1α,3β,21-trihydroxy-9,10-seco-5,7,10(19)-pregnatrien-20-one (a) Diisopropylamine (10.93 g) was dissolved in tetrahydrofuran (80 ml) and the solution was cooled to −78° C. To the cooled solution, 64 ml (96 mmol) of 1.5M-butyl lithium solution in hexane was slowly added. The reaction temperature was raised to −20° C., then chilled down to −78° C. Subsequently, 11.24 g of methyl methoxyacetate was added dropwise over a period of 30 minutes. The temperature was raised to −65° C., then further increased to −60° C. over a period of 40 minutes. The temperature was again chilled to −78° C. and a solution in tetrahydrofuran (20 ml) of 1α,3β-bis(tert-butyldimethylsilyloxy)-5,7-androstadien-17-one (6.37 g) was added over a period of 30 minutes. While the temperature was held at between −65° C. and −55° C., the reaction mixture was stirred for 3 hours, which was then immediately poured into water and subjected to three extractions with ethyl acetate. The combined extract were dried over sodium sulfate and the solvent was distilled off. The residue was purified by silica gel column chromatography (elution with 30% ethyl acetate-hexane) to obtain 5.32 g of methyl 1α,3β-bis(tert-butyldimethylsilyloxy)-17β-hydroxy-20-methoxy-5,7,pregnadien-21-oate.

NMR spectrum δ: 0.07 (3H,s), 0.08 (3H,s), 0.09 (3H,s), 0.13 (3H,s), 0.84 (3H,s), 0.88 (9H,s), 0.90 (12H,s), 2.70–2.84 (1H,m), 3.34 (3H,s), 3.70 (1H,bs), 3.79 (1H,s), 3.80 (3H,s), 3.91–4.11 (1H,m), 5.30 (1H,dt,J=5.7 and 2.3Hz). 5.56 (1H,d,J=5.7 Hz).

(b) A portion (5.10 g) of the compound obtained in (a) was dissolved in 40 ml of pyridine and the solution was cooled to −40° C. Thionyl chloride (2.9 ml) was slowly added dropwise with a syringe. After stirring the solution for 2 hours at −20° C., the mixture was immediately poured into aqueous sodium chloride. After extraction with 300 ml of ethyl acetate, the extract was washed with aqueous sodium chloride twice. The extract was then dried over sodium sulfate. After removal of the solvent under vacuum, the residue was purified by column chromatography (solvent: 10% ethyl acetate-hexane) to obtain 2.37 g of methyl 1α,3β-bis(tert-butyldimethylsilyloxy)-20-methoxy-5,7,17(20)-pregnatrien-21-oate, with recovery of 1.60 g of the starting material.

NMR spectrum δ(CDCl$_3$): 0.05 (3H,s), 0.06 (6H,s), 0.11 (3H,s), 0.88 (12H,s), 0.89 (9H,s), 0.92 (3H,s), 2.29–2.89 (6H,m), 3.57 (3H,s), 3.70 (1H,bs), 3.78 (3H,s), 3.93–4.15 (1H,m), 5.39 (1H,dt,J=5.7 and 2.9 Hz), 5.59 (1H,d,J=5.7 Hz).

(c) The compound (2.34 g) obtained in (b) was dissolved in 30 ml of hexane and the solution was cooled to −40° C. To the solution, 15.2 ml (15.2 mmol) of a solution of diisobutylaluminum hydride in hexane was slowly added dropwise with a syringe. After completion of the addition, the temperature of the solution was elevated to −20° C., at which temperature it was stirred for 1 hour. After dropwise addition of water (2 ml), the temperature of the solution was slowly raised to 0° C. The reaction mixture was poured into aqueous sodium chloride and extracted three times with ethyl acetate. The combined extract was dried over sodium sulfate and the solvent was distilled off. The residue was purified by silica gel column chromatography (elution with 30% ethyl acetate-hexane) to obtain 1.84 g of 1α,3β-bis(tert-butyldimethylsilyloxy)-20-methoxy-5,7,17(20)-pregnatrien-21-ol.

NMR spectrum δ(CDCl$_3$): 0.05 (3H,s), 0.06 (3H,s), 0.07 (3H,s), 0.11 (3H,s), 0.84 (3H,s), 0.88 (18H,s), 0.92 (3H,s), 2.20–2.57 (6H,m), 2.74–2.89 (1H,m), 3.55 (3H,s), 3.71 (1H,bs), 3.45–4.19 (1H,m), 4.13–4.28 (2H,m), 5.36 (1H,dt, J=5.7 and 2.9 Hz), 5.58 (1H,d,J=5.7 Hz).

(d) A portion (324 mg) of the compound obtained in (c) and 1.6 g of oxalic acid dihydrate were suspended in 70 ml of methanol and 7 ml of water. The suspension was stirred for 3 hours at 50°–55° C. After cooling, the reaction mixture was poured into about 500 ml of aqueous sodium chloride and extracted five times with ethyl acetate. The extracts were combined and washed with a saturated aqueous solution of sodium hydrogencarbonate. The organic layer was further washed with saturated aqueous sodium chloride. After drying over sodium sulfate, the concentrate was purified by silica gel column chromatography (elution with 50% ethyl acetatehexane) to obtain 226 mg of 1α-tert-butyldimethylsilyloxy-3β,21-dihydroxy-5,7-pregnadien-20-one.

NMR spectrum δ(CDCl$_3$): 0.06 (3H,s), 0.14 (3H,s), 0.61 (3H,s), 0.89 (21H,s), 2.58 (1H,t,J=8.5 Hz), 2.83 (1H,dist,t,J=8.6 Hz), 3.26 (1H,dist,t, J=4.6 Hz, disappears with D$_2$O), 3.75 (1H,bs), 3.94–4.16 (2H, one of them disappears with D$_2$O), 4.21 (2H,bs), 5.36 (1H,dt,J=5.7 and 2.9 Hz), 5.62 (1H,dd,J=2.7 and 2.6 Hz).

(e) The compound (270 mg) obtained in (d) was dissolved in 2 ml of dimethylformamide, and after addition of imidazole (560 mg) and tert-butyldimethylsilyl chloride (500 mg), the solution was stirred. After addition of tetrahydrofuran (3 ml), the mixture was further stirred for 30 minutes. The mixture was dissolved in 300 ml of hexane and washed three times with aqueous sodium chloride. After back extraction from the aqueous layer, the organic layers were combined and dried over sodium sulfate. The residue left after distilling off the solvent was purified by silica gel column chromatography (elution with chloroform) to obtain 299 mg of 1α,3β,21-tris(tert-butyldimethylsilyloxy)-5,7-pregnadien-20-one.

NMR spectrum δ:(CDCl$_3$): 0.05 (3H,s), 0.06 (3H,s), 0.07 (3H,s), 0.08 (6H,s), 0.11 (3H,s), 0.59 (3H,s), 0.88 (9H,s), 0.89 (12H,s), 0.92 (9H,s), 2.75–2.90 (1H,m), 2.85 (1H,t,J=8.6 Hz), 3.71 (1H,bs), 3.91–4.14 (1H,m), 4.17 (1H,d,J=17.7 Hz), 4.21 (1H,d,J=17.7 Hz), 5.34 (1H,dt,J=5.7 and 2.3 Hz), 5.58 (1H,d,J=5.7 Hz).

(f) A portion (178 mg) of the compound obtained in (e) was dissolved in 400 ml of hexane, and the solution was irradiated under a 200 W high-pressure mercury lamp for 36 minutes. Subsequently, the solvent was concentrated to half its initial volume and the solution was refluxed for 1 hour. After distilling off the excess solvent, the residue was roughly purified by silica gel column chromatography (elution with chloroform) to obtain a mixture of the starting material and a desired vitamine D derivative. The mixture was treated with 600 μl of trifluoroacetic acid in 3 ml of THF and 3 ml of methanol for 8 hours. With cooling the reaction mixture on an ice-bath, 1 g of sodium hydrogen carbonate was added. After stirring for 15 minutes at room temperature, the mixture was filtered. The residue left after distilling off the solvent was purified by preparative TLC (elution with 10% MeOH—CHCl$_3$) to obtain 2.3 mg of 1α,3β,21-trihydroxy-9,10-seco-5,7,10(19)-pregnatrien-20-one.

NMR spectrum δ(CDCl$_3$) 0.53 (3H,s), 2.52–2.68 (2H,m), 2.87 (1H,dist,d,J=12 Hz), 3.26 (2H,bs), 4.12–4.34 (4H,m), 4.38–4.49 (1H,m), 4.98 (1H,t,J=1.7 Hz), 5.33 (1H,t,J=1.7 Hz), 6.05 (1H,d,J=10.8 Hz), 6.34 (1H,d,J=10.8 Hz).

UV spectrum (EtOH): λ$_{max}$=262 nm.

EXAMPLE 12

Preparation of 9,10-seco-5,7,10(19)-pregnatriene-1α,3β,20β,20-tetraol

A portion (3.7 mg) of the 1α,3β,21-trihydroxy-9,10-seco-5,7,10(19)-pregnatrien-20-one obtained in Example 11(f) was dissolved in 3 ml of isopropanol. After cooling the solution to 0° C., 10 mg of sodium borohydride was added. After stirring the mixture for 15 minutes at 0° C., the mixture was warmed to room temperature and further stirred for 1 hour. After addition of 100 l of water, the solvent was distilled off and the residue was subjected to preparative TLC (solvent: 10% methanol-chloroform), whereby 1.7 mg of crude 9,10-seco-5,7,10(19)-pregnatriene-1α,3β,20β,21-tetraol was obtained. This crude product was further purified on a flash column (elution with ethyl acetate) to obtain the pure product in an amount of 1.55 mg.

NMR spectrum δ(CDCl$_3$): 0.65 (3H,s), 2.32 (1H,dd, J=12.5 and 6.3 Hz), 2.59 (1H,dd,J=12.5 and 3.4 Hz), 2.85 (1H,dd,J=11.4 and 2.8 Hz), 3.32–3.48 (1H,m), 3.57–3.76 (2H,m), 4.16–4.30 (1H,m), 4.37–4.48 (1H,m), 4.99 (1H,t,J=1.4 Hz), 5.32 (1H,t,J=1.4 Hz), 6.01 (1H,d,J=11.2 Hz), 6.36 (1H,d,J=11.2 Hz).

UV spectrum (EtOH): λmax=264 nm

EXAMPLE 13

Preparation of 1α,3β,17,21-tetrahydroxy-9,10-seco-5,7,10(19)-pregnatrien-20-one (a) A portion (330 mg) of the 1α,3β-bis(tert-butyldimethylsilyloxy)-20-methoxy-5,7,17(20)-pregnatrien-21-ol obtained in Example 11(c) was dissolved in 200 ml of dichloromethane. To the solution, a solution in dichloromethane (20 ml) of m-chloroperbenzoic acid (100 mg) was added dropwise at −74° C. over a period of 40 minutes. After stirring the solution at −74° C. for 1 hour, the temperature of the solution was gradually raised to 5° C. over a period of 3 hours. Then, after adding 5 g of sodium hydrogencarbonate, the solution was stirred vigorously. The cooling bath was removed and the solution was further stirred for 15 minutes. The reaction mixture was subjected to filtration and the filterate was concentrated. The residue was subjected to preparative TLC (solvent: 30% ethyl acetate-hexane), whereby 187 mg of 1α,3β-bis(tert-butyldimethylsilyloxy)-17,21-dihydroxy-5,7-pregnadien-20-one was obtained.

NMR spectrum δ(CDCl$_3$): 0.06 (3H,s), 0.07 (3H,s), 0.10 (3H,s), 0.13 (3H,s), 0.63 (3H,s), 0.88 (12H,s), 0.90 (9H,s), 2.24–2.90 (4H,m), 3.11 (1H,t,J=5.1 Hz), 3.42 (1H,s), 3.70 (1H,bs), 3.92–4.14 (1H,m), 4.36 (1H,dd,J=20.5 and 5.1 Hz), 4.68 (1H,dd,J=20.5 and 5.1 Hz), 5.37 (1H,dt, J=5.7 and 2.9 Hz), 5.58 (1H,d,J=5.7 Hz).

(b) The compound (204 mg) obtained in (a) was dissolved in dimethylformamide (8 ml) and tetrahydrofuran (12 ml), and after addition of imidazole (470 mg) and tert-butyldimethylsilyl chloride (500 mg), the mixture was stirred for 30 minutes at room temperature. The reaction mixture was dissolved in 300 ml of hexane and the solution was washed with aqueous sodium chloride three times. After back extraction from the aqueous layer with hexane, the organic layers were combined and dried over sodium sulfate. The residue left after distilling off the solvent was purified by silica gel column chromatography (elution with 10% ethyl acetate-hexane) to obtain 208.3 mg of 1α,3β,21-tris(tert-butyldimethylsilyloxy)-17-hydroxy-5,7-pregnadien-20-one.

NMR spectrum δ(CDCl$_3$): 0.05 (3H,s), 0.07 (3H,s), 0.08 (3H,s), 0.12 (6H,s), 0.13 (3H,s), 0.63 (3H,s), 0.88 (12H,s), 0.89 (9H,s), 0.94 (9H,s), 2.26–2.88 (4H,m), 3.66 (1H,bs), 3.71 (1H,bs), 3.92–4.14 (1H,m), 4.48 (2H,s), 5.35 (1H,dt, J=5.7 and 2.9 Hz), 5.58 (1H,d,J=5.7 Hz).

(c) A portion (104 mg) of the compound obtained in (b) was dissolved in 400 ml of hexane. While being bubbled through with argon gas, the solution was irradiated with a 200 W high-pressure mercury lamp for 20 minutes. After being concentrated to half its volume, the hexane solution was refluxed for 1 hour in a nitrogen atmosphere. The same reaction was repeated and the two reaction mixtures were combined. After distilling off the solvent, the residue was subjected to silica gel column chromatography and eluted with chloroform. The effluent crude product was dissolved in methanol (10 ml) and tetrahydrofuran (10 ml), and after addition of 2 ml of trifluoroacetic acid, the mixture was stirred for 23 hours at room temperature. Following addition of sodium hydrogencarbonate (5 g), the mixture was vigorously stirred for 15 minutes. The reaction mixture was subjected to filtration and the solvent was distilled off. The residue was subjected to preparative TLC (solvent: 15% methanol-chloroform), whereby 57.3 mg of the desilyl form of the starting compound was recovered.

The active fractions containing the desired vitamin D derivative were subjected to preparative TLC (solvent: 15% methanol-hexane), whereby about 7 mg of crude 1α,3β,17,21-tetrahydroxy-9,10-seco-5,7,10(19)-pregnatrien-20-one was obtained. The crude product was subjected to another run of preparative TLC (solvent: ethyl acetate) to obtain 1.0 mg of the pure form of the desired compound.

NMR spectrum δ(CDCl₃): 0.58 (3H,s), 2.35 (1H,dd, J=12.5 and 6.3 Hz), 2.55-2.96 (4H,m), 3.10 (1H,t, J=4.9 Hz), 4.21-4.31 (1H,m), 4.35 (1H,dd,J=20.0 and 4.9 Hz), 4.38-4.51 (1H,m), 4.66 (1H,dd,J=20.0 and 4.9 Hz), 5.01 (1H,t,J=1.5 Hz), 5.35 (1H,t, J=1.5 Hz), 6.09 (1H,d,J=11.4 Hz), 6.38 (1H,d, J=11.4 Hz).

UV spectrum (EtOH): $\lambda_{max}$=264 nm

EXAMPLE 14

Preparation of 9,10-seco-5,7,10(19)-pregnatriene 1α,3β,17,20β,21-pentaol (a) A portion (100 mg) of 1α,3β-bis(tert-butyldimethyl-silyloxy)-17,21-dihydroxy-5,7-pregnadien-20-one obtained in Example 13(a) was dissolved in 8 ml of isopropanol and the solution was cooled to 0° C. After addition of 20 mg of sodium borohydride, the solution was vigorously stirred for 1 hour. Water (0.1 ml) was added and the solution was stirred for 30 minutes. Following addition of ethyl acetate (200 ml), the mixture was washed with saturated aqueous sodium chloride. After back extraction from the aqueous layer, the organic layers were combined and dried over sodium sulfate. The residue left after distilling off the solvent was subjected to preparative TLC (solvent: 65% ethyl acetate-hexane) to obtain 59 mg of 1α,3β-bis(tert-butyldimethylsilyloxy)-5,7-pregnadiene-17,20β,21-triol.

NMR spectrum δ(CDCl₃): 0.06 (3H,s), 0.07 (3H,s), 0.08 (3H,s), 0.11 (3H,s), 0.75 (3H,s), 0.88 (18H,s), 0.92 (3H,s), 2.27-3.04 (7H,m), 3.56-3.91 (4H,m), 3.91-4.15 (1H,m), 5.32 (1H,dt,J=5.7 and 2.9 Hz), 5.58 (1H,d,J=5.7 Hz).

(b) The compound (59 mg) obtained in (a) was dissolved in 400 ml of ethanol. While being bubbled through with an argon gas, the solution was irradiated with a 200 W high-pressure mercury lamp for 35 minutes. The reaction mixture was directly refluxed for 1.5 hours. After distilling off the solvent, the residue was subjected to preparative TLC (solvent: 65% ethyl acetate-hexane), whereby 38.1 mg of a mixture of the starting material and a desired vitamin D derivative was obtained. After drying under vacuum, the mixture was dissolved in 1.2 ml of tetrahydrofuran and mixed with 0.3 ml (0.3 mmol) of a solution of tetrabutylammonium fluoride in tetrahydrofuran, followed by stirring for 24 hours. The reaction mixture was directly subjected to preparative TLC (solvent: 15% methanol-chloroform) to obtain 6.0 mg of 9,10-seco-5,7,10(19)-pregnatriene-1α,3β,17,20β,21-pentaol. This crude product was further purified by preparative TLC (solvent: 5% methanol-ethyl acetate).

NMR spectrum δ(CDCl₃): 0.68 (3H,s), 3.70-3.86 (3H,m), 4.16-4.29 (1H,m), 4.37-4.47 (1H,m), 4.99 (1H,t, J=1.6 Hz), 5.32 (1H,t,J=1.6 Hz), 6.03 (1H,d, J=11.4 Hz), 6.36 (1H,d,J=11.4 Hz).

UV spectrum (EtOH): $\lambda_{max}$=263 nm

EXAMPLE 15

Preparation of 9,10-seco-5,7,10(19)-pregnatriene-1α,3β,20β-triol

A portion (4.7 mg) of the 1α,3β-dihydroxy-9,10-secO-5,7,10(19)-pregnatrien-20-one obtained in Example 6(b) was treated as in Example 12 to obtain 1.42 mg of 9,10-seco-5,7,10(19)-pregnatriene-1α,3β,20β-triol.

NMR spectrum δ(CDCl₃): 0.63 (3H,s), 1.15 (3H,d, J=5.7 Hz), 2.31 (1H,dd,J=13.1 and 6.3 Hz), 2.59 (1H,dd,J=13.1 and 3.4 Hz), 2.85 (1H,dd,J=10.8 and 2.9 Hz), 3.71 (1H,dq,J=9.1 and 5.7 Hz), 4.16-4.30 (1H,m), 4.36-4.48 (1H,m), 4.99 (1H,t,J=1.5 Hz), 5.31 (1H,t,J=1.5 Hz), 6.00 (1H,d,J=11.4 Hz), 6.37 (1H,d,J=11.4 Hz).

UV spectrum (EtOH): $\lambda_{max}$=264 nm.

EXAMPLE 16

Preparation of 9,10-seco-5,7,10(19)-pregnatriene-1α,3β,20αtriol (a) Starting from 1α,3β-bis(tert butyldimethylsilyloxy)-5,7-androstadien-17-one, the procedures described in Example 9(b) and (c) were followed, whereby 1 α,3β-bis(tert-butyl-dimethylsilyloxy)-5,7-pregnadien-20α-ol was obtained.

NMR spectrum δ(CDCl₃): 0.05 (3H,s), 0.06 (6H,s), 0.11 (3H,s), 0.62 (3H,s), 0.88 (18H,s), 0.90 (3H,s), 1.24 (3H,d,J=5.7 Hz), 2.71-2.85 (1H,m), 3.62-3.79 (2H,m), 3.92-4.11 (1H,m), 5.32 (1H,dt, J=5.7 and 2.9 Hz), 5.58 (1H,d,J=5.7 Hz).

(b) Sixty milligrams of the compound obtained in (a) was dissolved in 400 ml of ethanol. While being bubbled through with an argon gas, the solution was irradiated with a 200 W high-pressure mercury lamp for 42 minutes. Subsequent procedures were followed as in Example 14(b) to obtain 7.2 mg of 9,10-seco-5,7,10(19)-pregnatriene-1α,3β,20α-triol.

NMR spectrum δ(CDCl₃): 0.55 (3H,s), 1.23 (3H,d, J=6.6 Hz), 2.33 (1H,dd,J=13.1 and 6.0 Hz), 2.61 (1H,dd,J=13.1 and 2.9 Hz), 2.85 (1H,dd,J=10.8 and 2.9 Hz), 3.71 (1H,quint,J=6.6 Hz), 4.17-4.31 (1H,m), 4.37-4.51 (1H,m), 5.00 (1H,t,J=1.4 Hz), 5.33 (1H,t,J=1.4 Hz), 6.04 (1H,d,J=11.7 Hz), 6.37 (1H,d, J=11.7 Hz).

UV spectrum (EtOH): $\lambda_{max}$=263 nm

EXAMPLE 17

Preparation of 20α-(3-hydroxy-3-methylbutyloxy)-9,10,seco-5,7,10(19)-pregnatriene-1α,3β-diol (a) Three hundred milligrams of the 1α,3β-bis(tert-butyldimethylsilyloxy)-5,7-pregnadien-20α-ol obtained in Example 16(a) was dissolved in 10 ml of xylene, and after addition of sodium hydride (500 mg) and 1-bromo-3-propene (6.0 g), the solution was refluxed for 18 hours. Then, water (200 μl) was added and the solution was stirred. The solids content was removed by silica gel column chromatography (eluted with ethyl acetate). The solvent was distilled off and the residue was subjected to preparative TLC (solvent: 4% ethyl acetate-hexane) to obtain 200 mg of a mixture containing 20α-(3-butenyloxy)-1α,3β-bis(tert-butyldimethylsilyloxy)-5,7-pregnadiene. This mixture was directly dissolved in 20 ml of dimethylformamide, followed by addition of water (0.5 ml). After addition of cuprous chloride (29 mg) and palladium dichloride (17 mg), the solution was vigorously agitated for 19 hours in an oxygen atmosphere. The metal salts were removed by Florisil ® column chromatography (solvent: 1:1 mixture of ethyl acetate and hexane). The eluate was diluted with 300 ml of a 1:1 mixture of ethyl acetate and hexane, and the solution was washed with aqueous sodium chloride three times. After back extraction from the aqueous layer, the organic layers were combined and dried over sodium sulfate. After distilling off the solvent, the residue was subjected to preparative TLC, whereby 70 mg of 1α,3β-bis(tertbutyldimethylsilyloxy)-20α-(3-oxobutyloxy)-5,7-pregnadiene was obtained.

NMR spectrum δ(CDCl₃): 0.05 (3H,s), 0.06 (3H,s), 0.07 (3H,s), 0.10 (3H,s), 0.58 (3H,s), 0.88 (18H,s), 0.89 (3H,s), 1.16 (3H,d,J=5.7 Hz), 2.18 (3H,s), 2.28–2.38 (2H,m), 2.56–2.68 (2H,m), 2.68–2.84 (1H,m), 3.16–3.34 (1H,m), 3.52 (1H,dt, J=9.7 and 6.4 Hz), 3.65–3.72 (1H,m), 3.80 (1H,dt, J=9.7 and 6.4 Hz), 5.31 (1H,dt,J=5.7 and 2.9 Hz), 5.57 (1H,d,J=5.7 Hz).

(b) The compound (73 mg) obtained in (a) was dissolved in 4 ml of tetrahydrofuran and the solution was ice-cooled. After addition of 0.3 ml (0.9 mmol) of a solution of methyl magnesium bromide in ether, the solution was stirred for 1 hour with ice-cooling. The reaction mixture was poured into aqueous sodium chloride and subjected to extraction with 200 ml of ethyl acetate. The extract was washed with aqueous sodium chloride and the combined aqueous layers were subjected to back extraction. The organic layers were combined and dried over sodium sulfate. The solvent was distilled off and the residue was subjected to preparative TLC (solvent: 25% ethyl acetate-hexane) to obtain 45.8 mg of 1α,3β-bis(tert-butyldimethylsilyloxy)-20α-(3-hydroxy-3-methylbutyloxy)-5,7-pregnadiene.

NMR spectrum δ(CDCl₃): 0.06 (3H,s), 0.07 (6H,s), 0.11 (3H,s), 0.61 (3H,s), 0.88 (18H,s), 0.90 (3H,s), 1.21 (3H,d,J=6.3 Hz), 1.23 (3H,s), 1.24 (3H,s), 2.27–2.38 (2H,m), 2.67–2.86 (1H,m), 3.26 (1H,quint,J=6.3 Hz), 3.49 (1H,dt,J=9.1 and 5.4 Hz), 3.66–3.72 (1H,m), 3.72–3.90 (1H,m), 3.90–4.14 (1H,m), 5.31 (1H,dt,J=5.7 and 2.3 Hz), 5.57 (1H,d,J=5.7 Hz).

(c) A portion (43 mg) of the compound obtained in (b) was dissolved in 400 ml of ethanol. While being bubbled through with an argon gas, the solution was irradiated with a 200 W high-pressure mercury lamp for 35 minutes. The reaction mixture was directly refluxed for 2 hours under nitrogen atmosphere. The solvent was distilled off and the residue was passed through a flash column (solvent: 25% ethyl acetate-hexane) to obtain 7 mg of a fraction containing vitamin D derivative as the main component and 30 mg of a fraction consisting predominantly of the starting material. The latter fraction was dissolved in ethanol (400 ml) and likewise subjected to irradiation and passed through a flash column, whereby 16 mg of a fraction containing vitamin D derivative was obtained. This fraction was combined with the previously obtained active fraction (7 mg) and dried under vacuum. The concentrate was then dissolved in 1 ml of tetrahydrofuran and combined with 0.11 ml (0.11 mmol) of a solution of tetrabutylammonium fluoride in tetrahydrofuran, followed by agitation for 19 hours at room temperature. To the mixture, another 0.11 ml (0.11 mmol) of a solution of tetrabutylammonium fluoride in tetrahydrofuran was added and the resultant mixture was stirred for 4 hours. The reaction mixture was directly subjected to preparative TLC (solvent: ethyl acetate) to obtain 6.6 mg of 1α-hydroxy-20α-(3-hydroxy-3-methylbutyloxy)-9,10-seco-5,7,10(19)-pregnatriene. This crude product was further purified by flash column chromatography (solvent: 10% chloroform-ethyl acetate).

NMR spectrum δ(CDCl₃): 0.54 (3H,s), 1.18 (3H,d, J=6.3 Hz), 1.23 (6H,s), 2.31 (1H,dd,J=13.7 and 6.6 Hz), 2.60 (1H,dd,J=13.7 and 3.4 Hz), 2.82 (1H,dd,J=12.0 and 1.7 Hz), 3.25 (1H,quint, J=6.3 Hz), 3.47 (1H,dt,J=9.1 and 5.4 Hz), 3.75–3.91 (2H,m), 4.16–4.30 (1H,m), 4.36–4.50 (1H,m), 4.98 (1H,t,J=1.4 Hz), 5.32 (1H,t,J=1.4 Hz), 6.02 (1H,d,J=11.4 Hz), 6.36 (1H,d,J=11.4 Hz)

UV spectrum (EtOH): λ$_{max}$=263 nm.

What is claimed is:

1. A vitamin D derivative of the formula:

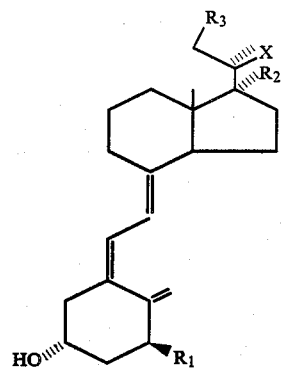

where $R_1$, $R_2$ and $R_3$, which may be the same or different, each represents a hydrogen atom or a hydroxyl group; X is an oxygen atom, the group of the formula OR₄ (where R₄ is either a hydrogen atom or a lower alkyl group having 4 to 6 carbon atoms that may or may not be substituted by a hydroxyl group), or the group of the formula N—OR₅ (where R₅ is either a hydrogen atom or a lower alkyl group having 1 to 5 carbon atoms that may or may not be substituted by a hydroxyl group, an amino group or a lower alkylamino group having 1 3 carbon atoms), provided that the carbon atom at the 20-position in linked to X by a single bond when X is the group of the formula OR₄, and by a double bond in other cases, with the proviso that X is not an oxygen atom or a hydroxyl group when all or $R_1$, $R_2$ and $R_3$ are hydrogen.

2. A vitamin D derivative in accordance with claim 1 which is represented by the formula:

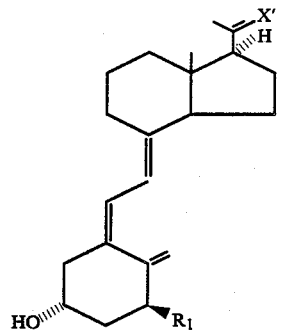

where X′ is either an oxygen atom or a group of the formula N—OR₅, with the proviso that R₁ is not hydrogen when X′ is oxygen.

3. A vitamin derivative in accordance with claim 1 which is represented by the formula:

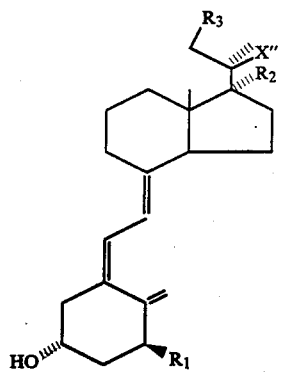

where at least one of $R_2$ and $R_3$ is a hydroxyl group; and X" is either an oxygen atom or a hydroxyl group, provided that the carbon atom at the 20-position is linked to X" by a single bond when X" is a hydroxyl group, and by a double bond when X" is an oxygen atom.

4. A vitamin D derivative in accordance with claim 3, wherein X" is a hydroxyl group.

5. A vitamin D derivative in accordance with claim 4, wherein $R_1$, $R_2$ and $R_3$ are all hydroxyl groups.

6. A therapeutic composition for the treatment of disorders in the immune system, comprising a pharmaceutically acceptable carrier, and, as an active ingredient, an effective amount of vitamin D derivative in accordance with claim 1.

7. A composition in accordance with claim 6, wherein, in said vitamin D derivative, $R_2$ and $R_3$ are hydrogen and X is either an oxygen atom or a group of the formula N—$OR_5$, with the proviso that $R_1$ is not hydrogen wherein X is oxygen.

8. A composition in accordance with claim 6, wherein, in said vitamin D derivative, at least one of $R_2$ and $R_3$ is a hydroxyl group and X is either an oxygen atom or a hydroxyl group.

9. A composition in accordance with claim 8, wherein, in said vitamin D derivative, $R_1$ is a hydroxyl group.

10. A composition in accordance with claim 8, wherein, in said vitamin D derivative, X is a hydroxyl group.

11. A composition in accordance with claim 10, wherein, in said vitamin D derivative, $R_1$, $R_2$, and $R_3$ are all hydroxyl groups.

12. A composition in accordance with claim 6, wherein, in said vitamin D derivative, X is a group of the formula $OR_4$.

13. In the method for including differentiation in tumor cells or treating disorders of the immune system by administering an effective amount of a derivation of vitamin $D_3$, the improvement whereby the effect of such administration on calcium metabolism in vivo is minimized, wherein said vitamin $D_3$ derivative is a compound in accordance with claim 1.

14. A method according with claim 13, wherein, in said compound, $R_2$ and $R_3$ are hydrogen and X is either an oxygen atom or a group of the formula N—$OR_5$, with the proviso that $R_1$ is not hydrogen when X is oxygen.

15. A method in accordance with claim 13, wherein, in said compound, at least one of $R_2$ and $R_3$ is a hydroxyl group and X is either an oxygen atom or a hydroxyl group.

16. A method in accordance with claim 15, wherein, in said compound, $R_1$ is a hydroxyl group.

17. A method in accordance with claim 15, wherein, in said compound, X is a hydroxyl group.

18. A method in accordance with claim 17, wherein, in said compound, $R_1$, $R_2$, and $R_3$ are all hydroxyl groups.

19. A method in accordance with claim 13, wherein, in said compound, X is a group of the formula $OR_4$.

20. A method for inducing differentiation of tumor cells, which tumor cells can have differentiation induced by vitamin $D_3$, without substantially affecting the in vivo calcium metabolism of the patient, comprising:
administering to a patient in need of such treatment an effective amount of a vitamin D derivative in accordance with claim 1.

21. A method for treating disorders of the immune system, which disorders are treatable by vitamin $D_3$, without substantially affecting the in vivo calcium metabolism of the patient, comprising:
administering to a patient in need of such treatment an effective amount of a vitamin D derivative in accordance with claim 1.

22. A vitamin D derivative of the formula:

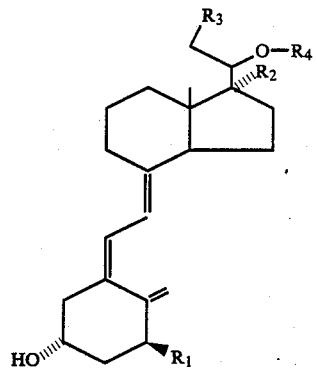

wherein $R_1$, $R_2$, and $R_3$ which may be the same or different, each represents a hydrogen atom or a hydroxyl group; and $R_4$ is a hydrogen atom or a lower alkyl group having 4–6 carbon atoms that may or may not be substituted by a hydroxyl group.

23. A vitamin D derivative of the formula:

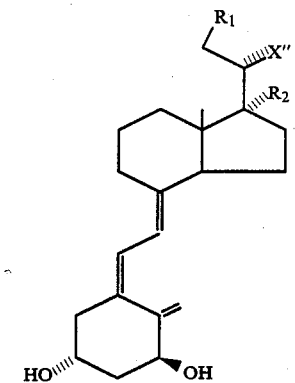

where $R_2$ and $R_3$ each represents a hydrogen atom or a hydroxyl group and at least one of $R_2$ and $R_3$ is a hydroxyl group; and X" is an oxygen atom or a hydroxyl group, provided that the carbon atom at the 20-position is linked to X" by a single bond when X" is a hydroxyl group, and by a double bond when X" is an oxygen atom.

* * * * *

UNITED STATES PATENT AND TRADEMARK OFFICE
CERTIFICATE OF CORRECTION

PATENT NO. : 4,891,364

DATED : January 2, 1990

INVENTOR(S) : KUBODERA et al.

It is certified that error appears in the above-identified patent and that said Letters Patent is hereby corrected as shown below:

Column 35, line 56    Delete "1a-hydroxy-20a", insert therefor -- 1α,3β-dihydroxy-20α --

Signed and Sealed this

Fourth Day of February, 1992

Attest:

HARRY F. MANBECK, JR.

*Attesting Officer*                    *Commissioner of Patents and Trademarks*